US011009504B2

(12) United States Patent
Koo et al.

(10) Patent No.: US 11,009,504 B2
(45) Date of Patent: May 18, 2021

(54) SYSTEM AND METHOD FOR PERFORMING AN ASSAY WITH SUB-PIXEL SIZED BEADS

(71) Applicant: Maxim Integrated Products, Inc., San Jose, CA (US)

(72) Inventors: Ronald B. Koo, Los Altos, CA (US); Henry Grage, Johns Creek, GA (US)

(73) Assignee: Maxim Integrated Products. Inc., San Jose, CA (US)

( * ) Notice: Subject to any disclaimer, the term of this patent is extended or adjusted under 35 U.S.C. 154(b) by 227 days.

(21) Appl. No.: 15/883,159

(22) Filed: Jan. 30, 2018

(65) Prior Publication Data
US 2018/0217134 A1   Aug. 2, 2018

Related U.S. Application Data

(60) Provisional application No. 62/452,715, filed on Jan. 31, 2017.

(51) Int. Cl.
*G01N 33/543*   (2006.01)
*G06T 7/00*   (2017.01)
*G01N 33/53*   (2006.01)

(52) U.S. Cl.
CPC ... *G01N 33/54306* (2013.01); *G01N 33/5304* (2013.01); *G01N 33/54313* (2013.01); *G01N 33/54373* (2013.01); *G06T 7/0016* (2013.01); *G06T 2207/30024* (2013.01)

(58) Field of Classification Search
None
See application file for complete search history.

(56) References Cited

U.S. PATENT DOCUMENTS

| 3,561,356 | A | * | 2/1971 | Rarey | G03G 17/00 101/129 |
| 4,197,088 | A | * | 4/1980 | Meserol | G01N 21/03 250/574 |
| 4,305,721 | A | * | 12/1981 | Bernstein | G01N 33/54313 422/565 |
| 4,769,404 | A | * | 9/1988 | Spadaro | G01N 33/54313 524/54 |
| 5,286,452 | A | * | 2/1994 | Hansen | G01N 33/4905 422/73 |

(Continued)

FOREIGN PATENT DOCUMENTS

| WO | 2010047804 A1 | 4/2010 |
| WO | WO-2015052162 A2 * | 4/2015 ............ B01L 3/5025 |

*Primary Examiner* — Matthew D Krcha
(74) *Attorney, Agent, or Firm* — Kevin E. West; Advent, LLP

(57) ABSTRACT

A sensor system that employs sub-pixel sized beads for assays is disclosed. The sensor system includes a first plurality of sensor pixels that define a first active sensor area. The first active sensor area is configured to receive a first portion of a fluid sample. The first portion is mixed with a plurality of first functionalized beads for performing a first assay. The sensor system also includes at least a second plurality of sensor pixels that define a second active sensor area. The second active sensor area is configured to receive a second portion of the fluid sample. The second portion is mixed with a second plurality of functionalized beads for performing a second assay. The first assay and the second assay may be configured to detect different concentration ranges of an analyte in the fluid sample.

22 Claims, 18 Drawing Sheets

(56) References Cited

U.S. PATENT DOCUMENTS

| | | |
|---|---|---|
| 2002/0102578 A1 | 8/2002 | Dickinson |
| 2004/0018629 A1* | 1/2004 | Kawate .............. G01N 15/1468 |
| | | 436/63 |
| 2004/0197821 A1 | 10/2004 | Bauer |
| 2007/0238140 A1* | 10/2007 | Pentoney, Jr. ... G01N 33/54313 |
| | | 435/7.92 |
| 2012/0044339 A1* | 2/2012 | Stith .................. G01N 21/6458 |
| | | 348/79 |
| 2014/0308690 A1 | 10/2014 | Samproni |

* cited by examiner

SYSTEM AND METHOD FOR PERFORMING AN ASSAY WITH SUB-PIXEL SIZED BEADS

CROSS-REFERENCE TO RELATED APPLICATIONS

The present application claims the benefit under 35 U.S.C. § 119(e) of U.S. Provisional Application Ser. No. 62/452,715, filed Jan. 31, 2017, and titled "SYSTEM AND METHOD FOR PERFORMING AN ASSAY WITH SUB-PIXEL SIZED BEADS," which is incorporated herein by reference in its entirety.

BACKGROUND

The determination of components in biological fluids (e.g., blood, urine, etc.) and other materials (e.g., gas samples, etc.) is continuing to increase in importance. Biological fluid tests can be used in a health care environment to determine physiological and/or biochemical states, such as disease, mineral content, pharmaceutical drug effectiveness, and/or organ function. For example, it may be desirable to determine an analyte concentration within an individual's blood to manage a health condition, such as diabetes. Consequently, the individual may be required to go to a diagnostic laboratory or medical facility to have blood drawn and then wait (often for an extended period) for analysis results, which can be inconvenient. Moreover, the individual must often schedule a follow-up visit with a healthcare provider to review the analysis results, which can also add cost. For these reasons and others, there is an increasing need for devices that can facilitate point of care testing.

BRIEF DESCRIPTION OF THE DRAWINGS

The detailed description is described with reference to the accompanying figures. The use of the same reference numbers in different instances in the description and the figures may indicate similar or identical items. Various embodiments or examples ("examples") of the present disclosure are disclosed in the following detailed description and the accompanying drawings. The drawings are not necessarily to scale. In general, operations of disclosed processes may be performed in an arbitrary order, unless otherwise provided in the claims.

DETAILED DESCRIPTION

Overview

Figure 1A:
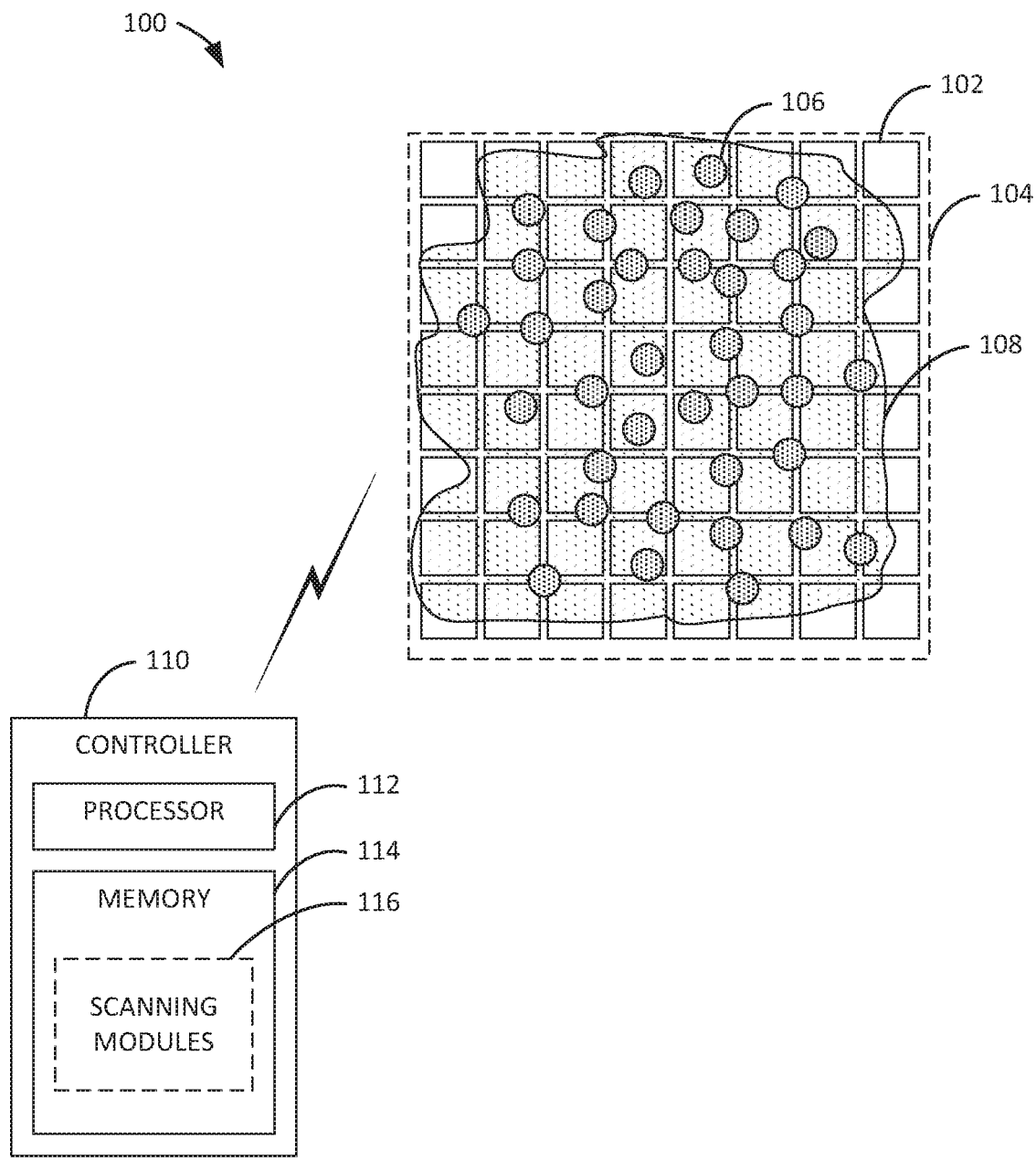
FIG. 1A is a schematic of a sensor having at least one active sensor area with functionalized beads for performing an agglutination assay, in accordance with an example embodiment of the present disclosure.

An assay is a test performed by adding one or more reagents to a sample (e.g., a fluid sample, such as a biological liquid or gas) and analyzing how the sample or the reagents are consequently affected. For example, functionalized beads (e.g., beads comprising or coated with one or more reagents) may agglutinate when a certain analyte is present in the fluid sample. Some examples of assays are agglutination or agglomeration assays including, but not limited to, immunoassays, kinetic agglutination assays, agglomeration-of-beads assays, kinetic agglomeration-of-beads assays, coagulation assays, kinetic coagulation assays, surface antigen assays, receptor assays from biopsy procedures, circulating blood cells assays, or circulating nucleic acid assays.

A system and method are disclosed for performing assays with sub-pixel sized beads (e.g., functionalized beads). In embodiments, a system can include a sensor (e.g., electric-field sensor, magnetic-field sensor, optical sensor, multimodal sensor, or the like) that has a plurality of sensor pixels formed by at least one array or matrix of sensor elements. The array or matrix of sensor elements can define an active sensor area that is configured to receive a fluid sample. The fluid sample can be mixed with a plurality of functionalized beads for performing an assay. In embodiments, the functionalized beads can be mixed into (e.g., dissolved into) the fluid sample in proximity to the active sensor area. For example, the functionalized beads can be mixed into the fluid sample at the active sensor area or near the active sensor area (e.g., in a chamber adjacent to the active sensor area). A functionalized bead of the plurality of functionalized beads can have a cross-sectional area smaller than a pixel area of a sensor pixel. Consequently, individual functionalized beads may be invisible to (e.g., undetectable to) the sensor. The functionalized beads can become visible (e.g., detectable by the sensor) when they agglutinate and form one or more agglomerations (sometimes referred to herein as "clumps") that cover at least a threshold portion of a respective pixel area of a sensor pixel.

In embodiments, a sensor assembly includes a chamber configured to receive a fluid sample. The chamber can include a first active sensor area disposed in a first portion of the chamber and configured to receive a first portion of the fluid sample. The first active sensor area includes a first plurality of sensor pixels, where each sensor pixel defines a first pixel area. The first active sensor area also includes first functionalized beads having a cross-sectional area that is smaller than the first pixel area and having a first coating configured to cause agglutination of a plurality of the first functionalized beads when a target analyte is present in the first portion of the fluid sample. In some embodiments, the chamber further includes at least one second active sensor area disposed in a second portion of the chamber and configured to receive a second portion of the fluid sample. The second active sensor area includes a second plurality of sensor pixels, where each sensor pixel defines a second pixel area. The second active sensor area also includes second functionalized beads having a cross-sectional area that is smaller than the second pixel area and having a second coating configured to cause agglutination of a plurality of the second functionalized beads when the target analyte is present in the second portion of the fluid sample. The first and second sensor pixels are communicatively coupled to a controller configured to: receive electrical signals from the first and second plurality of sensor pixels; process the electrical signals to determine whether the electrical signals from a subset of the first plurality of sensor pixels indicate agglutination of the plurality of the first functionalized beads and to determine whether the electrical signals from a subset of the second plurality of sensor pixels indicate agglutination of the plurality of second functionalized beads; determine a concentration of the target analyte in the fluid sample based on the agglutination of the plurality of the first functionalized beads, the agglutination of the plurality of the second functionalized beads, or both; and generate data representing the concentration of the target analyte.

In some embodiments, the first active sensor area and the second active sensor area can be configured to detect different concentration ranges of an analyte in the fluid sample. In some embodiments, the sensor can include a third active sensor area, and possibly more. The sensor can be used to perform multiple assays (at the different active sensor areas) to detect different concentration ranges of an analyte and/or different analytes in the fluid sample by using respective sets of functionalized beads, where each set of functionalized beads can be configured to agglutinate in the presence of a threshold concentration of an analyte.

Example Implementations

Embodiments of a sensor 100 are shown in FIGS. 1A through 7B. In these embodiments, the sensor 100 includes a plurality of sensor elements 102 that define at least one active sensor area 104. Sensor elements 102 defining active sensor area 104 are sometimes referred to herein as "sensor pixels 102." Each sensor pixel 102 defines a respective pixel area. For example, a pixel area for a sensor pixel 102 can correspond to a portion of active sensor area 104 occupied by the sensor pixel 102. Sensor pixels 102 can generate electrical signals based on sensed impedances or changes in impedance, sensed capacitances or changes in capacitance, sensed changes in magnetic field, sensed light scattering, reflection, or refraction, and combinations thereof. Example sensor elements 102 may employ metal panels, coils, photodetectors, or a combination thereof, and so forth. For example, in an embodiment, a sensor pixel 102 can include a metal panel configured to generate one or more electrical signals associated with an impedance or capacitance or a change in impedance or capacitance that is sensed by the metal panel. In this regard, each sensor pixel 102 can be configured to generate an electrical signal indicating a change in an electric field (e.g., a horizontal electric field, a vertical electric field, and/or an oscillating electric field). In some embodiments, the electric field is an oscillating electric field having a frequency in the range of 1 megahertz (MHz) and 300 MHz. In another embodiment, a sensor pixel 102 can include a coil configured to generate one or more electrical signals associated with a change in magnetic field that is sensed by the coil. In yet another embodiment, a sensor pixel 102 can include a photodetector configured to generate one or more electrical signals associated with scattered, reflected, or refracted light that is sensed by the photodetector. In some embodiments, sensor pixels 102 can also include two or more sets or arrays of different sensor elements (e.g., metal panels and coils, metal panels and photodetectors, coils and photodetectors, or a combination of all three sensor elements). Further examples of an electric field sensor (wherein sensor pixels 102 include metal panels), a magnetic field sensor (wherein sensor pixels 102 include coils), an optical sensor (wherein sensor pixels 102 include photodetectors), and a multi-modal sensor (wherein sensor pixels 102 are defined by a combination of different types of sensor elements) are described in U.S. patent application Ser. No. 15/244,600, which is incorporated herein by reference in its entirety. Embodiments of the sensor 100 may include any of the sensor embodiments disclosed in U.S. patent application Ser. No. 15/244,600.

Figure 2A:
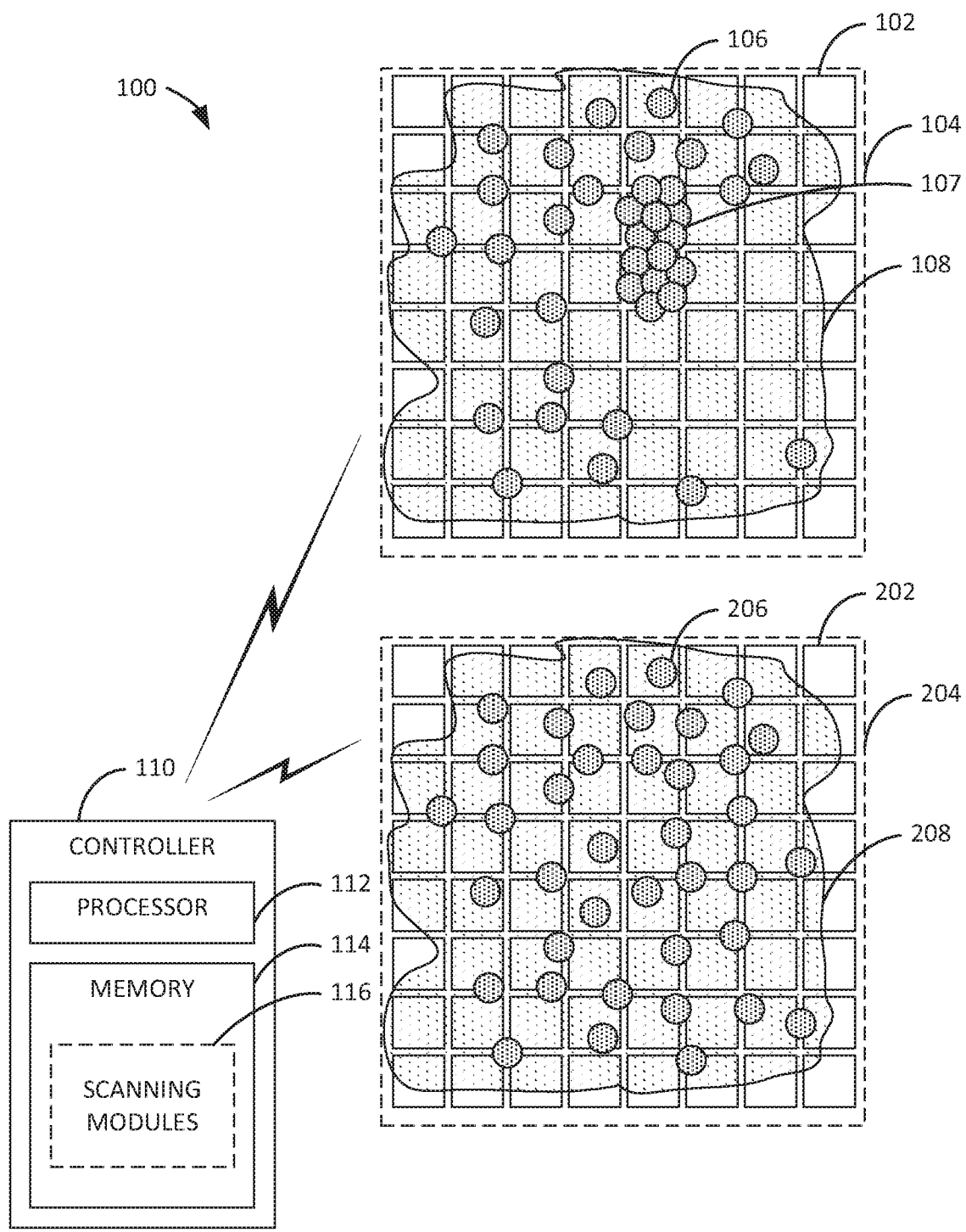
FIG. 2A is a schematic of a sensor having at least two active sensor areas with functionalized beads configured to receive fluid samples for performing agglutination assays, in accordance with an example embodiment of the present disclosure, wherein the functionalized beads at a first active sensor area have formed an agglomeration and the functionalized beads at a second active sensor area are dispersed.

As shown in FIG. 1A, active sensor area 104 is configured to receive a portion 108 of a fluid sample. The portion 108 of the fluid sample can include one or more analytes (e.g., hormones, proteins, viruses, prions, sperm, cells, biological microparticles, etc.). The portion 108 of the fluid sample can be mixed with functionalized beads 106 in order to perform one or more assays for the one or more analytes. In embodiments, a functionalized bead 106 can have a cross-sectional area smaller than a respective pixel area defined by a sensor pixel 102, such that the sensor pixel 102 is configured to detect an agglomeration 107 of functionalized beads 106 in proximity to the sensor pixel 102 when the agglomeration 107 covers at least a threshold portion of the respective pixel area. For example, a sensor pixel 102 may be configured to detect an agglomeration of functionalized beads 106 when the agglomeration 107 covers a respective pixel area of the sensor pixel 102 as is shown in FIG. 2A, or when the agglomeration 107 covers a threshold percentage (e.g., 50% or more) of the respective pixel area.

Figure 1B:
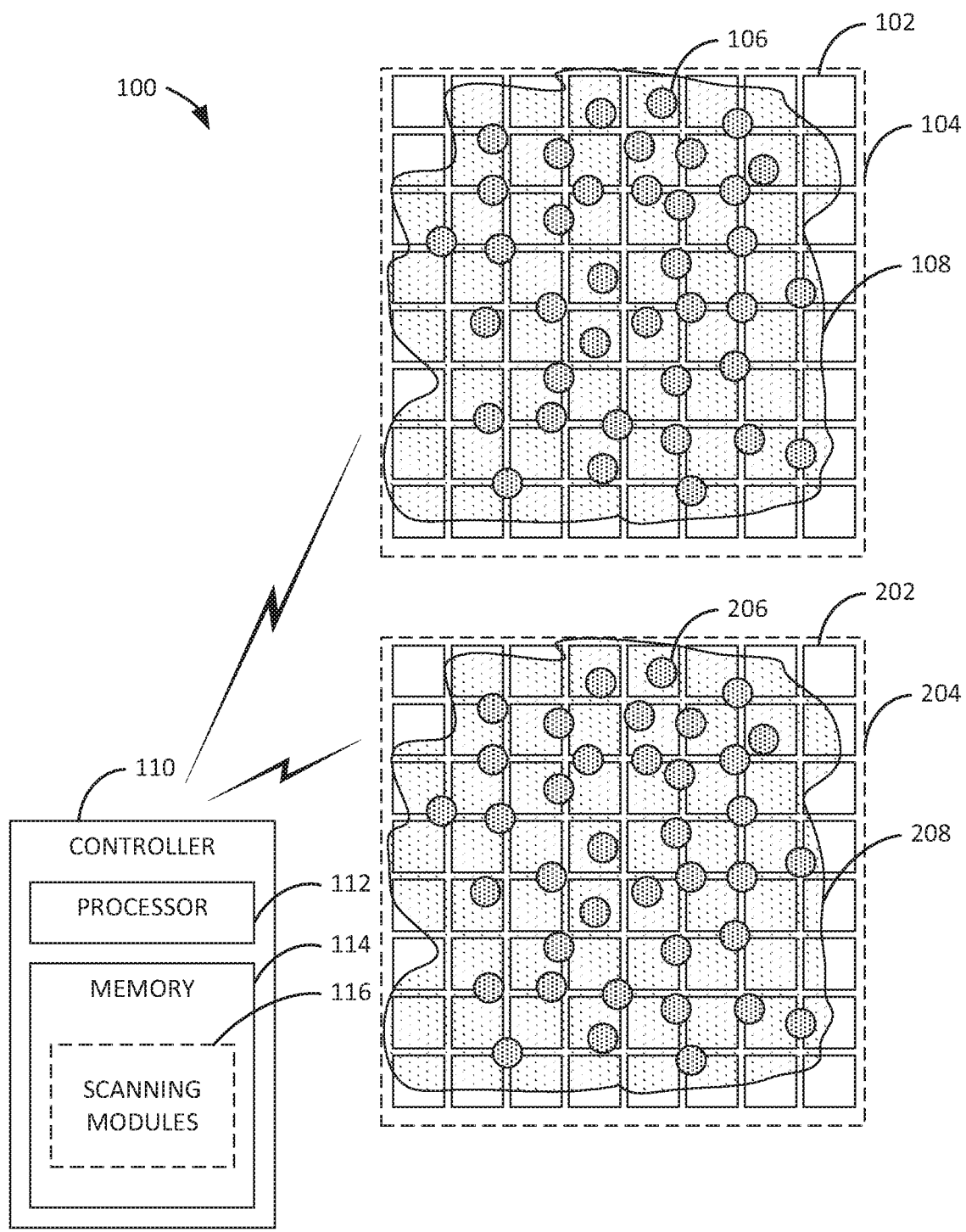
FIG. 1B is a schematic of a sensor having at least two active sensor areas with functionalized beads configured to receive fluid samples for performing agglutination assays, in accordance with an example embodiment of the present disclosure, wherein the functionalized beads at a first active sensor area and a second active sensor area are dispersed.

In an embodiment shown in FIG. 1B, the sensor 100 further includes a second plurality of sensor pixels 202 that define a second active sensor area 204. The second active sensor area 204 can be configured to receive a second portion 208 of the fluid sample. The second portion 208 of the fluid sample may be mixed with a second plurality of functionalized beads 206 for performing a second assay. In some implementations, the first assay and the second assay can be configured to detect different concentration ranges of an analyte in the fluid sample. In some implementations, the first assay and the second assay can be configured to detect different analytes. In some embodiments, the sensor 100 can further include a third active sensor area, and possibly more. The sensor 100 can be used to perform multiple assays (at the different active sensor areas) to detect different concentration ranges of an analyte and/or different analytes in the fluid sample by using respective sets of functionalized beads, where each set of functionalized beads can be configured to agglutinate in the presence of a threshold concentration of an analyte. The sensor 100 can include any number of active sensor areas, results of which can be compared against one another or combined to increase dynamic range of the sensor 100 (e.g., by employing assays configured to detect different concentration ranges of one or more analytes). In some embodiments, the first active sensor area 104 is configured to perform a first assay and the second active sensor area 204 is configured to perform a second assay, where the first assay and the second assay are sensitive to different ranges of concentrations of the target analyte. There are several configurations by which the first active sensor area 104 and the second active sensor area 204 can be tuned to detect different ranges of the concentration of a target analyte. For example, the first functionalized beads 106 may have different dimensions (e.g., can be larger or smaller) than the second functionalized beads 206 in order to detect the different ranges of concentrations of the target analyte. In embodiments, the first functionalized beads 106 may have different physical parameters (e.g., different composition) than the second functionalized beads 206 in order to detect the different ranges of concentrations of the target analyte. The first functionalized beads 106 can be coated with a different reagent or a different amount of a reagent than the second functionalized beads 206 in order to detect the different ranges of concentrations of the target analyte. The first pixel area (e.g., area of each pixel 102) can be different from the second pixel area (e.g., area of each pixel 202) in order to detect the different ranges of concentrations of the target analyte. For example, the first pixel area may be larger than the second pixel area. In some embodiments, to implement different pixel areas for active sensor area 104 and active sensor area 204, each sensor pixel of the first plurality of sensor pixels that define active sensor area 104 may be a software-defined sensor pixel 118 that includes at least two sensor pixels 102 (e.g., as described herein and shown in FIG. 118).

Several analyses can be performed with functionalized beads 106 and functionalized beads 206. For example, functionalized beads 106 and functionalized beads 206 may also be useful in coagulation assays as image enhancers if red blood cells are difficult to resolve. Instead of relying solely on the red blood cells, the sensor 100 can be configured to image movement of beads along with the red blood cells as a clot is forming. Functionalized beads 106 and functionalized beads 206 can also be used as internal standards to help verify object sizes (e.g., size of blood cells when doing complete blood counts) because the beads are manufactured with a known size (e.g., known diameter or diameter within known range). In embodiments, functionalized beads 106 and functionalized beads 206 can include, but are not limited to: plastic (e.g., PolyStyrene (PS)) beads with, sizes (diameter) ranging from 50 nm to 13 µm; PS coated beads, sizes (diameter) ranging from 40 nm to 5 µm; PS coated beads, sizes (diameter) ranging from 5 um to 35 µm; ferromagnetic beads (e.g., chromium dioxide coated PS beads), sizes (diameter) ranging from 2 µm to 120 µm; paramagnetic beads (e.g., magnetite coated PS beads, possibly with variety of coatings), sizes (diameter) ranging from 100 nm to 120 µm; gold or silver colloids (particles/sols), sizes (diameter) ranging from 2 nm to 250 nm; or other commercially available beads. Examples of functionalized beads 106 and functionalized beads 206 can include, but are not limited to: Glass Particles by COSPHERIC, PolyStyrene Latex Beads by SIGMA ALDRICH, Polystyrene Particles by SPHEROTECH, INC., Paramagnetic Particles by SPHEROTECH, INC., Ferromagnetic Particles by SPHEROTECH, INC., Magnetic Microspheres by EMD MILLIPORE CORP., Gold Sols, a combination thereof, and so forth. In some embodiments, functionalized beads 106 and/or functionalized beads 206 can have diameters in the range of 390 nm to 700 nm (the wavelengths of visible light).

In embodiments, functionalized beads 106 are mixed with (e.g., dissolved into) the portion 108 of the fluid sample in proximity to active sensor area 104. For example, functionalized beads 106 can be mixed with the portion 108 of the fluid sample at active sensor area 104 or near active sensor area 104 (e.g., just prior to introducing the fluid sample 108 to active sensor area 104). Similarly, functionalized beads 206 can be mixed with (e.g., dissolved into) the portion 208 of the fluid sample in proximity to the active sensor area 204. For example, the functionalized beads 206 can be mixed with the portion 208 of the fluid sample at the active sensor area 204 or near the active sensor area 204 (e.g., just prior to introducing the fluid sample 208 to the active sensor area 204).

Figure 5A:
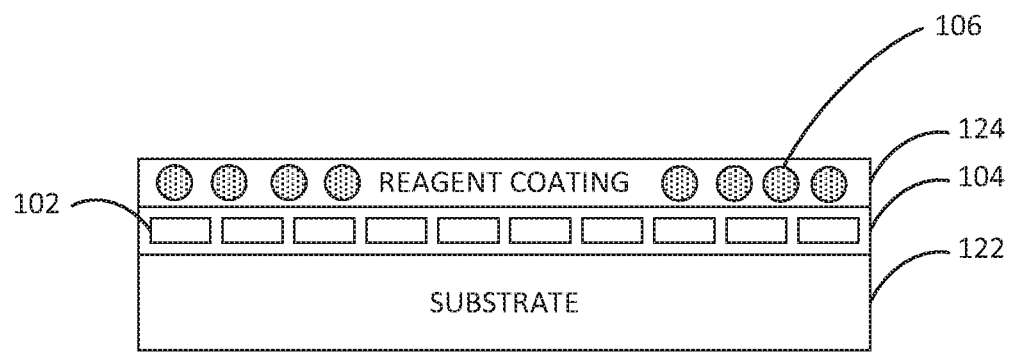
FIG. 5A is a cross-sectional side view of a sensor with a reagent coating disposed in proximity to an active sensor area of the sensor, in accordance with an example embodiment of the present disclosure, wherein the reagent coating includes functionalized beads for performing an agglutination assay.
Figure 5B:
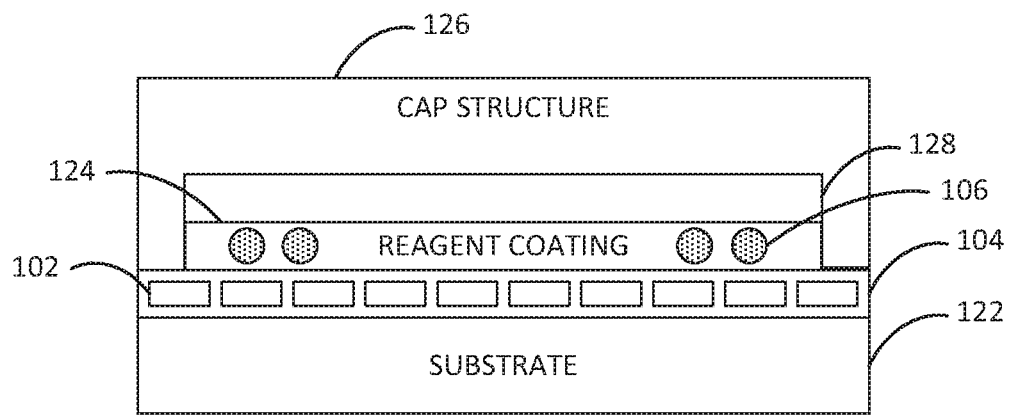
FIG. 5B is a cross-sectional side view of a sensor with a reagent coating disposed in proximity to an active sensor area of the sensor, in accordance with an example embodiment of the present disclosure, wherein the reagent coating includes functionalized beads for performing an agglutination assay, and wherein a cap structure covers at least a portion of the active sensor area.
Figure 5C:
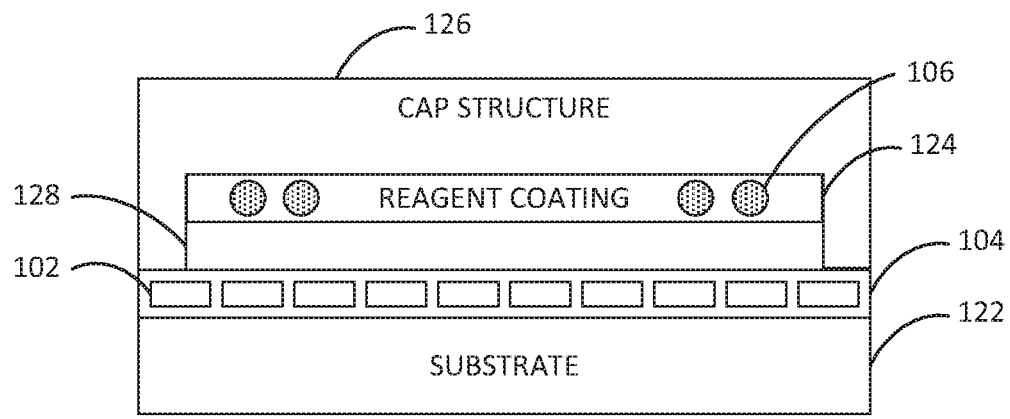
FIG. 5C is a cross-sectional side view of a sensor with a reagent coating disposed within an upper capillary space defined by a cap structure that covers at least a portion of an active sensor area of the sensor, in accordance with an example embodiment of the present disclosure, wherein the reagent coating includes functionalized beads for performing an agglutination assay.

FIGS. 5A through 5C show embodiments of a sensor cell that defines active sensor area 104. The second active sensor area 204 can also be included in a sensor cell that is similarly structured (not shown). The sensor 100 can include any number of sensor cells. As shown in FIGS. 5A and 5B, a reagent coating 124 that includes functionalized beads 106 can be disposed in proximity to (e.g., on top of) active sensor area 104. Active sensor area 104 can be supported by a substrate 122 (e.g., a silicon substrate or the like). As shown in FIG. 5B, active sensor area 104 can be covered by a cap structure 126. The cap structure 126 can be disposed upon the substrate 122, over active sensor area 104, such that the cap structure 126 (e.g., a microfluidic cap) and the active sensor area 104 define a chamber 128 configured to receive the fluid sample 108. In an embodiment shown in FIG. 5C, the reagent coating 124 can be disposed within the cap structure 126 (e.g., coated on an inner surface of the cap structure 126). In other embodiments, the reagent coating 124 can be disposed upon surfaces of both active sensor area 104 and the cap structure 126. In some embodiments, the sensor 100 can be implemented as a portable test strip. In some embodiments, the sample chamber 128 may be on the order of microns in order to be large enough for the fluid sample 108 (e.g., blood) to flow in but small enough to filter out cells (e.g., red blood cells) or only allow one or two layers of cells to be present. For example, the chamber 128 may have a height of 3 um or less.

Figure 6A:
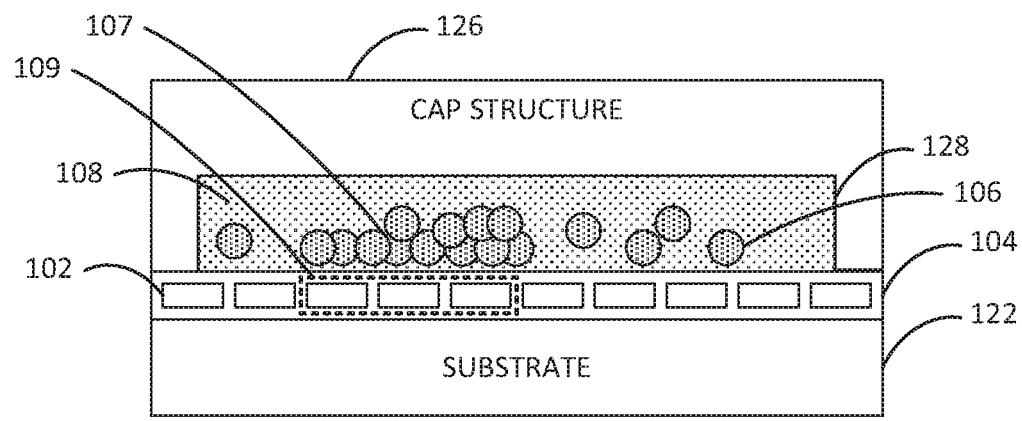
FIG. 6A is a side view of a sensor, such as the sensor illustrated in any of FIGS. 5A through 5C, wherein a fluid sample disposed in proximity to the active sensor area releases the functionalized beads from the reagent coating.

Functionalized beads 106, and possibly other reagents, can be dissolved into the fluid sample 108 when the fluid sample 108 is disposed upon active sensor area 104 and/or when the fluid sample 108 flows into the chamber 128. For example, as shown in FIG. 6A, functionalized beads 106 are released from the reagent coating 124 when the portion 108 of the fluid sample is disposed in proximity to active sensor area 104 (e.g., when the fluid flows into the chamber 128). Disposing functionalized beads 106 just above active sensor area 104 of the sensor 100 or near active sensor area 104 (e.g., in the cap structure 126) may reduce the number of functionalized beads 106 needed, thereby reducing cost.

Reactions in an assay can begin when functionalized beads 106 are added to the fluid sample 108. Consequently, interaction of functionalized beads 106 with the fluid sample 108 at active sensor area 104 determines the start of the reaction. The end of the reaction determination can be a set time after the start of the reaction; this can be determined in an algorithm learned by repeated testing of sensors with reference material. The sensor 100 scans the reaction between the start and the end of the reaction.

Figure 6B:
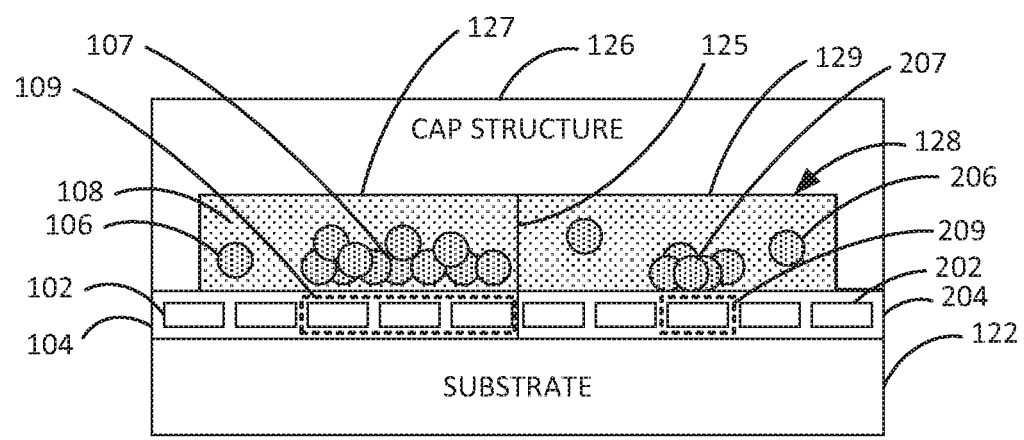
FIG. 6B is a side view of a sensor, such as the sensor illustrated in any of FIGS. 5A through 5C, wherein a fluid sample disposed in proximity to the active sensor area releases the functionalized beads from the reagent coating, and wherein the sensor includes at least a first active sensor area and a second active sensor area, for example, as illustrated in FIGS. 2A and 2B.

As shown in FIG. 6B, the chamber 128 may comprise multiple portions 127 and 129 or sub-chambers. For example, the chamber 128 may include a first portion 127 and a second portion 129 that are separated by at least one wall 125. In embodiments, the first active sensor area 104 is disposed in the first portion 127 of the chamber 128 and configured to receive the first portion 108 of the fluid sample, and the second active sensor area 204 is disposed in the second portion 129 of the chamber 128 and configured to receive the second portion 208 of the fluid sample.

Referring again to FIGS. 1A and 1B, the sensor 100 includes or is communicatively coupled to a controller 110. The controller 110 can be directly (e.g., wired) or indirectly (e.g., wirelessly) connected to sensor pixels 102 and sensor pixels 202. In some embodiments, the controller 110 is included in the sensor 100 structure. In other embodiments, the controller 110 includes a mobile device (e.g., smartphone or tablet) or desktop computing device that is configured to receive electrical signals from the sensor 100. The controller 110 can include a processor 112 (e.g., microprocessor, microcontroller, ASIC, programmable logic device, or the like) and a memory 114 coupled to the processor 112. The memory 114 can include a non-transitory storage device, such as, but not limited to, a flash drive, a solid-state disk (SSD), or a SD card. In some embodiments, the memory 114 can include a network or cloud storage that is communicatively coupled to the processor 112 via a wired or wireless connection protocol. The controller 110 can be configured to cause the sensor 100 to scan the active sensor area 104 with sensor pixels 102 and scan active sensor area 204 with sensor pixels 202. The controller 110 can be configured to cause the sensor 100 to scan the active sensor area 104 and active sensor area 204 according to one or more predefined or user programmed scanning modules 116 (e.g., one or more sets of program instructions) executed by the processor 112 from the memory 114. In embodiments, the controller 110 is configured to generate an image, mapping, or data structure associated with the electrical signals received from sensor pixels 102 and sensor pixels 202. For example, sensor pixels 102 and sensor pixels 202 can scan active sensor area 104 and active sensor area 204 and transmit electrical signals associated with one or more detected structures (e.g., agglomerations 107 of functionalized beads 106, or agglomerations 207 of functionalized beads 206, or agglomerations in other active sensor areas) to the controller 110. The controller 110 can then generate the image, mapping, or data structure based on the electrical signals received from sensor pixels 102 and sensor pixels 202. For example, the controller 110 can be configured to associate electrical signals received from respective ones of sensor pixels 102 and sensor pixels 202 with respective data points (e.g., respective image pixels of a generated image or mapping). In embodiments, the controller 110 can be configured to monitor a coverage or change in coverage of active sensor area 104 and active sensor area 204 by detecting agglomerations 107 and agglomerations 207 based on a sequence of images (e.g., video footage) of active sensor area 104 and active sensor area 204.

In some embodiments, the controller 110 is configured to receive electrical signals from the first and second plurality of sensor pixels 102 and 202. The controller 110 can be configured to process the electrical signals to determine whether the electrical signals from a subset 109 of the first plurality of sensor pixels 102 indicate agglutination of the plurality of the first functionalized beads 106 and to determine whether the electrical signals from a subset 209 of the second plurality of sensor pixels 202 indicate agglutination of the plurality of second functionalized beads 206. For example, in the embodiment illustrated in FIG. 6B, the subset 109 of sensor pixels 102 (e.g., one or more of sensor pixels 102) can indicate agglutination of the first functionalized beads 106 based on electrical signals corresponding to a detected agglomeration 107 of beads 106, and the subset 209 of sensor pixels 202 (e.g., one or more of sensor pixels 202) can indicate agglutination of the second functionalized beads 206 based on electrical signals corresponding to a detected agglomeration 207 of beads 206. The controller 110 can be configured to determine a concentration of the target analyte in the fluid sample based on the agglutination of the plurality of the first functionalized beads 106, the agglutination of the plurality of the second functionalized beads 206, or both. For example, the controller 110 can be configured to determine a concentration of the target analyte in a respective portion of the fluid sample that is disposed in the first active sensor area 104, the second active sensor area 204, or both. In some embodiments, concentration measurements from the first active sensor area 104 and the second active sensor area 204 may be averaged, aggregated, or one of the measurements may be selected based on consistency, conformity to reference data, or the like. In some embodiments, the controller 110 is configured to process the electrical signals to determine whether the electrical signals from one or more subsets (e.g., subset 109 and/o subset 209) of the plurality of sensor pixels are indicative of agglutination of the functionalized beads disposed adjacent to the one or more subsets. The controller 110 may be further configured to monitor the electrical signals over time to measure a rate of agglutination of the functionalized beads, and determine, based on the rate of agglutination, a concentration of the target analyte in the fluid sample (e.g., for each of the active sensor areas and/or subsets). The controller 110 can be configured to compare the concentration of the target analyte determined in each active sensor area with data representing a dynamic range for the target analyte and further configured to determine target analyte concentration in the fluid sample based on the active sensor areas for which the concentration of the target analyte was within the dynamic range of the target analyte.

Figure 2B:
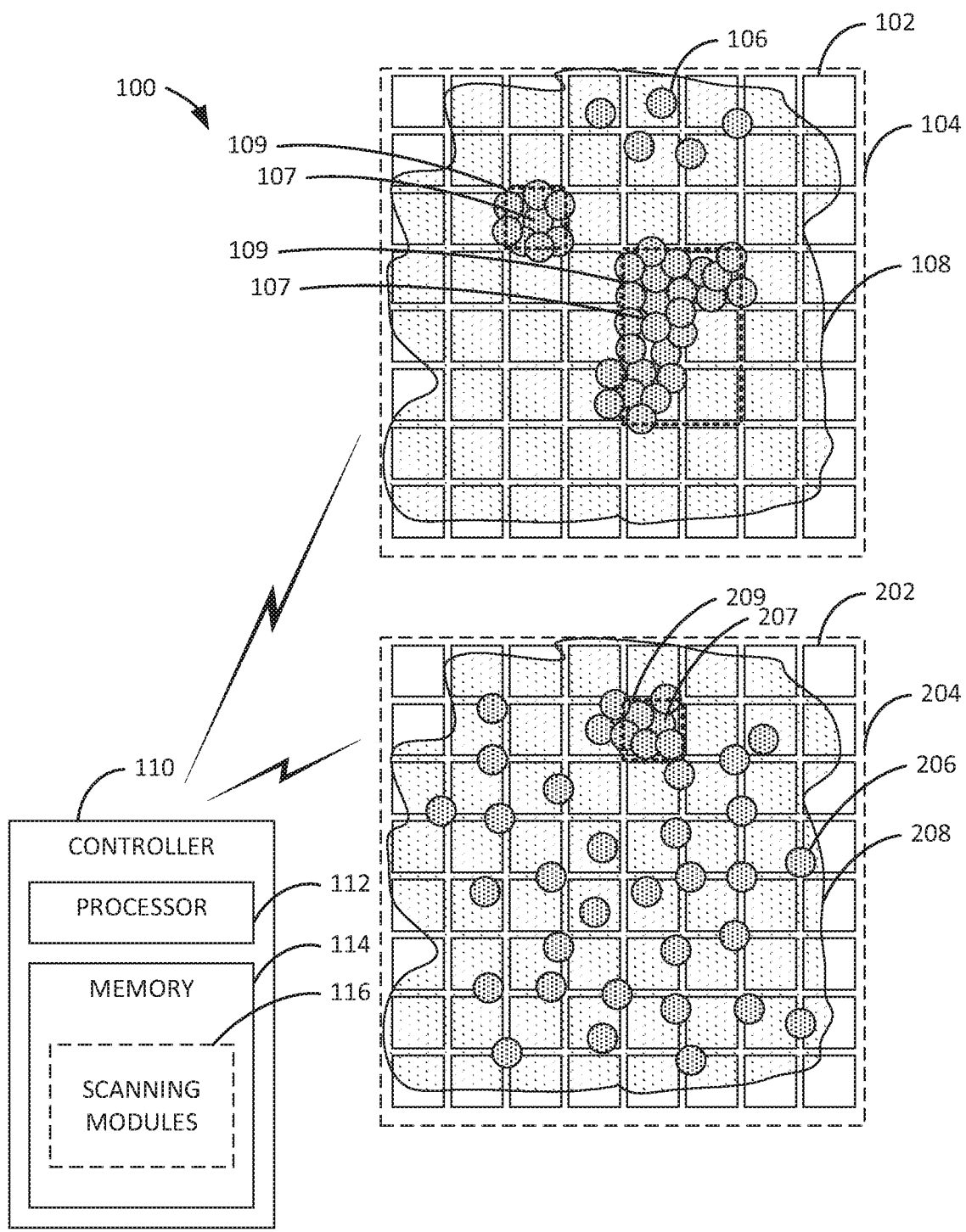
FIG. 2B is a schematic of a sensor having at least two active sensor areas with functionalized beads configured to receive fluid samples for performing agglutination assays, in accordance with an example embodiment of the present disclosure, wherein the functionalized beads at a first active sensor area have formed multiple agglomerations and the functionalized beads at a second active sensor area have formed a single agglomeration having a relatively lower level of coverage than the agglomerations at the first active sensor area.

In embodiments, the sensor 100 is configured to detect agglomerations 107 of functionalized beads 106 and agglomerations 207 of functionalized beads 206 when they achieve a threshold size that is detectable by one or more of sensor pixels 102 (or sensor pixels 202). For example, a sensor pixel 102 (or sensor pixel 202) can be configured to detect an agglomeration of functionalized beads when the agglomeration covers at least a threshold portion (e.g., 50% or more) of a respective pixel area of the sensor pixel 102 (or sensor pixel 202). As shown in FIGS. 1A and 1B, functionalized beads 106 and functionalized beads 206 can have respective cross-sectional areas smaller than the respective pixel areas of sensor pixels 102 and sensor pixels 202, and as a result, dispersed functionalized beads 106 and functionalized beads 206 may not be detectable by any of sensor pixels 102 or sensor pixels 202. For example, an individual functionalized bead 106 may not be detectable by a sensor pixel 102 when the functionalized bead does not cover a threshold portion of the respective pixel area of the sensor pixel 102. A plurality of functionalized beads 106 can become visible (e.g., detectable by the sensor 100) when they agglutinate and form one or more agglomerations 107 that cover at least a threshold portion of a respective pixel area of one of sensor pixels 102. For example, FIG. 2A shows an agglomeration 107 of functionalized beads 106 covering the respective pixel area of one sensor pixel 102 of active sensor area 104, while functionalized beads 206 over active sensor area 204 remain dispersed and are therefore undetectable. FIG. 2B shows detectable agglomerations 107 over active sensor area 104 that are comparatively larger than detectable agglomerations 207 over active sensor area 204. Such a scenario can indicate a stronger reaction (e.g., faster agglutination rate) for a first assay associated with functionalized beads 106, which may indicate higher sensitivity to a concentration of an analyte in the fluid sample.

In some embodiments, the controller 110 is configured to determine the concentration of the target analyte in the fluid sample at least partially based on a number of sensor pixels that indicate agglutination in a respective active sensor area. For example, the controller 110 can be configured to determine the concentration of the target analyte in the fluid sample at least partially by determining a number of sensor pixels in the subset (or subsets) 109 of the first plurality of sensor pixels 102 that indicate agglutination of the plurality of the first functionalized beads 106. In an embodiment, a sensor pixel 102 that generates an electrical signal having a signal strength (e.g., amplitude) above a threshold signal strength can indicate presence of an agglomeration 107 of beads 106 adjacent to the sensor pixel 102, thereby indicating agglutination. In some embodiments, the controller 110 can be configured to determine the concentration of the target analyte in the fluid sample at least partially by determining a number of sensor pixels in the subset (or subsets) 209 of the second plurality of sensor pixels 202 that indicate agglutination of the plurality of the second functionalized beads 206. In some embodiments, the controller 110 is configured to determine the concentration of the target analyte in the fluid sample at least partially by determining the number of sensor pixels in the subset (or subsets) 109 of the first plurality of sensor pixels 102 that indicate agglutination of the plurality of the first functionalized beads 106 and the number of sensor pixels in the subset (or subsets) 209 of the second plurality of sensor pixels 202 that indicate agglutination of the plurality of the second functionalized beads 206. For example, the results can be compared or quantified (e.g., averaged or aggregated) to determine the target analyte concentration.

In some embodiments, the controller 110 is configured to determine the concentration of the target analyte in the fluid sample at least partially based on a rate of agglutination. For example, the rate of agglutination can be the rate at which the coverage of agglutinating beads grows or the rate at which dispersion of beads in the fluid sample is reduced. The controller 110 can be configured to determine the concentration of the target analyte in the fluid sample at least partially by determining a first rate of agglutination corresponding to a number of sensor pixels in the subset (or subsets) 109 of the first plurality of sensor pixels 102 that indicate agglutination of the plurality of the first functionalized beads 106 over time. In another embodiment, the controller 110 can be configured to determine the concentration of the target analyte in the fluid sample at least partially by determining a second rate of agglutination corresponding to a number of sensor pixels in the subset (or subsets) 209 of the second plurality of sensor pixels 202 that indicate agglutination of the plurality of the second functionalized beads 206 over time. In some embodiments, the controller 110 is configured to determine the concentration of the target analyte in the fluid sample at least partially by determining a first rate of agglutination corresponding to the number of sensor pixels in the subset (or subsets) 109 of the first plurality of sensor pixels 102 that indicate agglutination of the plurality of the first functionalized beads 106 over time and a second rate of agglutination corresponding to the number of sensor pixels in the subset (or subsets) 209 of the second plurality of sensor pixels 202 that indicate agglutination of the plurality of the second functionalized beads 206 over time. For example, the results can be compared, averaged, or aggregated to determine the target analyte concentration. In some embodiments, the controller is configured to compare the first rate of agglutination, the second rate of agglutination, or both the first rate of agglutination and the second rate of agglutination with a reference data set or data plot (e.g., such as the data shown in FIG. 11 or 12) to determine the concentration of the target analyte in the fluid sample.

Rather than, or in addition to, determining a number of sensor pixels that indicate agglutination, the controller 110 can be configured to determine the concentration of the target analyte in the fluid sample at least in part by identifying and quantifying (e.g., averaging) signal measurements from adjacent sensor pixels. For example, the controller 110 can be configured to determine the concentration of the target analyte in the fluid sample at least in part by identifying and quantifying (e.g., averaging) signal measurements from adjacent sensor pixels 102 in the subset (or subsets) 109 of the first plurality of sensor pixels 102 that indicate agglutination of the plurality of the first functionalized beads 106, identifying and quantifying (e.g., averaging) signal measurements from adjacent sensor pixels 202 in the subset (or subsets) 209 of the second plurality of sensor pixels 202 that indicate agglutination of the plurality of the second functionalized beads 206, or both. In some embodiments, the controller 110 can be configured to determine the concentration of the target analyte in the fluid sample at least in part by determining a first rate of agglutination corresponding to quantified (e.g., averaged or aggregated) signal measurements from adjacent sensor pixels 102 in the subset (or subsets) 109 of the first plurality of sensor pixels 102 that indicate agglutination of the plurality of the first functionalized beads 106 over time and/or determining a second rate of agglutination corresponding to quantified (e.g., averaged or aggregated) signal measurements from adjacent sensor pixels 202 in the subset (or subsets) 209 of the second plurality of sensor pixels 202 that indicate agglutination of the plurality of the second functionalized beads 206 over time. In some embodiments, the controller is configured to compare the first rate of agglutination, the second rate of agglutination, or both the first rate of agglutination and the second rate of agglutination with a reference data set or data plot (e.g., such as the data shown in FIG. 11 or 12) to determine the concentration of the target analyte in the fluid sample.

Figure 3:
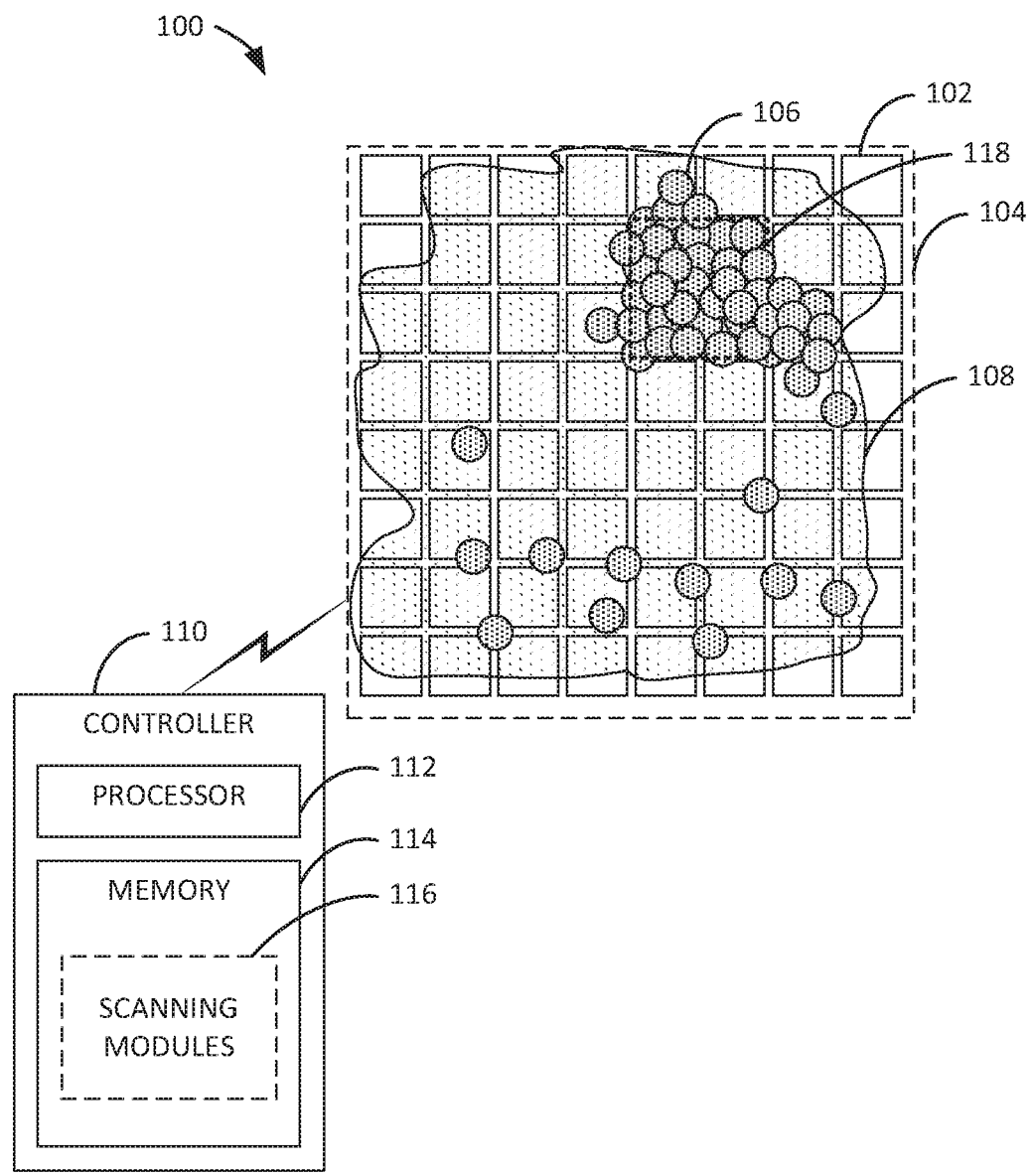
FIG. 3 is a schematic of a sensor having at least one active sensor area with functionalized beads for performing an agglutination assay, in accordance with an example embodiment of the present disclosure, wherein an agglomeration of functionalized beads is detectable by several sensor pixels of the active sensor area and/or at least one software defined sensor pixel including several sensor pixels of the sensor.

In some implementations, the scan pitch and/or pixel area can be adjusted by grouping two or more sensor pixels 102. For example, as shown in FIG. 3, two or more sensor pixels 102 can be configured as one (larger) software defined sensor pixel 118. In an embodiment, the first active sensor area 104 includes larger sensor pixels 102 than the sensor pixels 202 of the second active sensor area 204. In other embodiments, the first active sensor area 104 includes software defined pixels 118 (each including two or more sensor pixels 102), where the software defined pixels 118 are larger than the sensor pixels 202 of the second active sensor area 204. In some embodiments, the controller 110 is configured to combine (e.g., aggregate or average) electrical signals from two or more sensor pixels 102 in order to treat the electrical signals as having come from one software defined sensor pixel 118 including the two or more sensor pixels 102. For example, the controller 110 can combine electrical signals from groups of 4, 9, 16, ... $n^2$ sensor pixels 102 to achieve different pixel sizes. Groupings of squared numbers are provided by way of example; however, any groupings of two or more sensor pixels 102 can be implemented. By grouping sensor pixels 102 to define larger sensor pixels (e.g., software defined pixels 118), the controller 110 can cause the sensor 100 to scan active sensor area 104 at different sensor pitches. In some embodiments, the controller 110 can be configured to cause the sensor to perform progressively higher resolution scans. For example, the controller 110 can be configured to cause the sensor to perform a low resolution (large pixel) scan that can be performed at higher speed, followed by a higher resolution (small pixel) scan (e.g., to check for smaller agglomerations that cannot be detected at the low resolution scan). In some cases, multiple scan pitches may be implemented at the same active sensor area 104 in order to perform multiple assays with different response ranges. For example, two assays can be performed, where a first assay can have a first (lower) response range (e.g., generating small agglomerations) that may require smaller sensor pixels for detection, and a second assay can have second (higher) response range such that larger pixels can be used for detection. In this example, implementing larger software defined sensor pixels 118 for the second assay can help avoid interference from the first assay because the software defined sensor pixels 118 can be configured such that they do not detect and effectively filter out agglomerations of functionalized beads formed by the first assay. In an implementation, the sensor 100 can be configured to have multiple scan pitches for fetal viability assessment testing. For example, a sample tested in the lab with a result of "out of range—high" is typically diluted and rerun to obtain a quantitative result. Many assay kits have assay ranges of from 1 to 400 mIU/mL. Because hCG levels can go as high, in normal pregnancies, as 300,000 mIU/mL, these samples must be diluted by as much as 1:1,000 and rerun. Typically the dilutions are performed by making serial 1:10 dilutions of the sample and then testing each. So, this can result in as many as three additional assays needing to be run and processed. Using multiple scan pitches in active sensor area 104, it is possible to perform a single test (that is composed of multiple assay fields) that can cover a range of hCG levels—this can be done using a single blood sample in a single measurement procedure. By designing the assay fields with overlapping assay ranges, a range of normal hCG values from 2 to 300,000+ mIU/mL can be covered. Each assay range can cover a range of about two-and-a-half orders of magnitude. For example, the sensor 100 can be configured to implement three overlapping assay ranges: Assay Range #1: 2 to 300 mIU/mL; Assay Range #2: 100 to 15,000 mIU/mL; and Assay Range #3: 5,000 to 750,000 mIU/mL. These ranges are provided by way of example only and are not intended to limit the present disclosure in any way.

Figure 4:
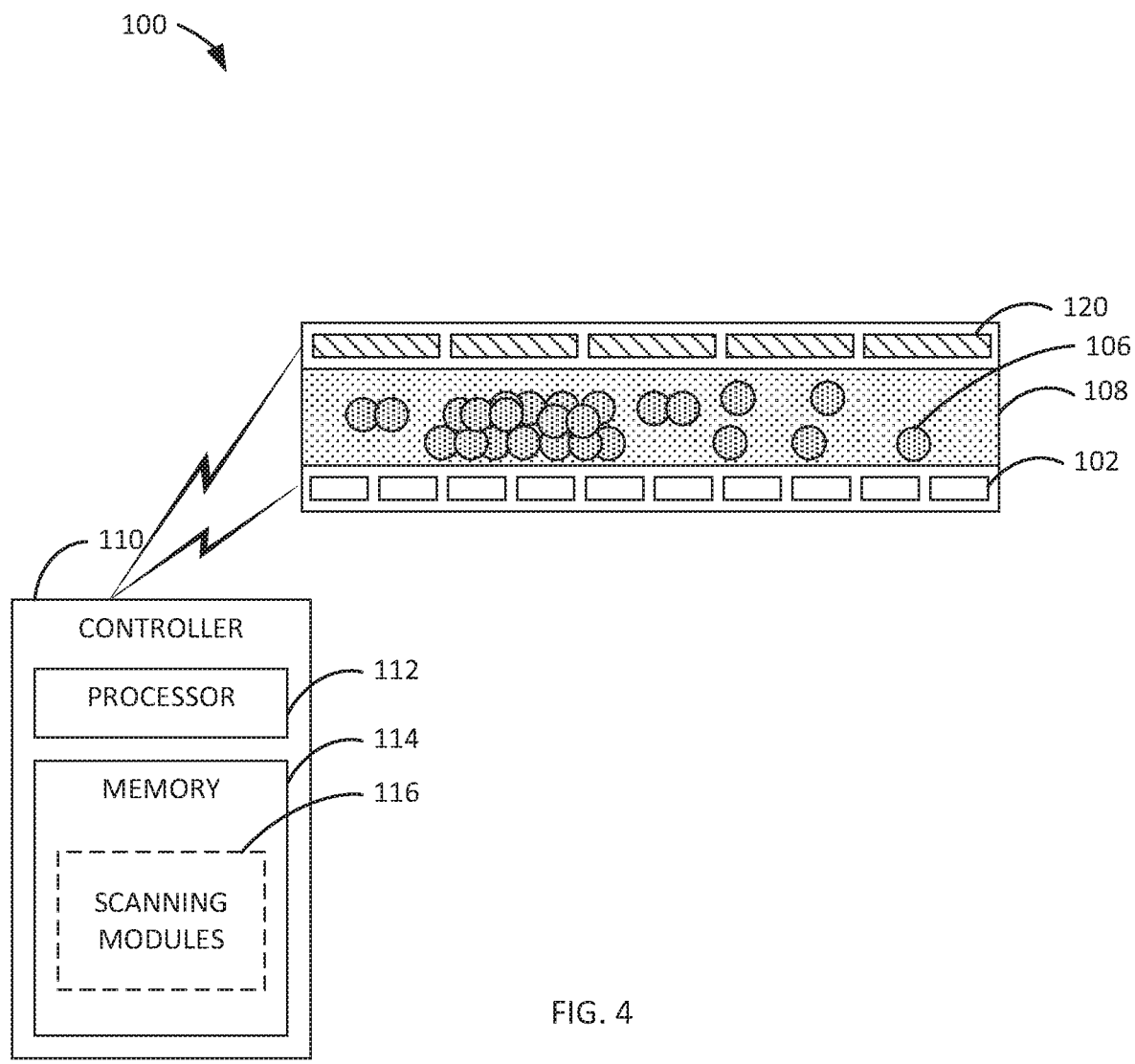
FIG. 4 is a schematic of a sensor having two active sensor areas configured to receive a fluid sample in between the two active sensor areas, wherein the two active sensor areas are on opposing surfaces and have differently sized sensor pixels, in accordance with an example embodiment of the present disclosure.

In an embodiment shown in FIG. 4, rather than implementing software defined pixels 118 (or in addition to the software defined pixels 118), the sensor 100 can include multiple active sensor areas (e.g., an active sensor area with smaller sensor pixels 102 and finer sensor pitch and at least a second active sensor area with larger sensor pixels 120 and coarser sensor pitch) configured to simultaneously receive a fluid sample 108. For example, the active sensor areas (e.g., active sensor area including sensor pixels 102 and active sensor area including sensor pixels 120) can be set on opposing surfaces (e.g., facing one another as shown in FIG. 4B, with a space for receiving the fluid sample 108 being in between the active sensor areas).

Figure 11:
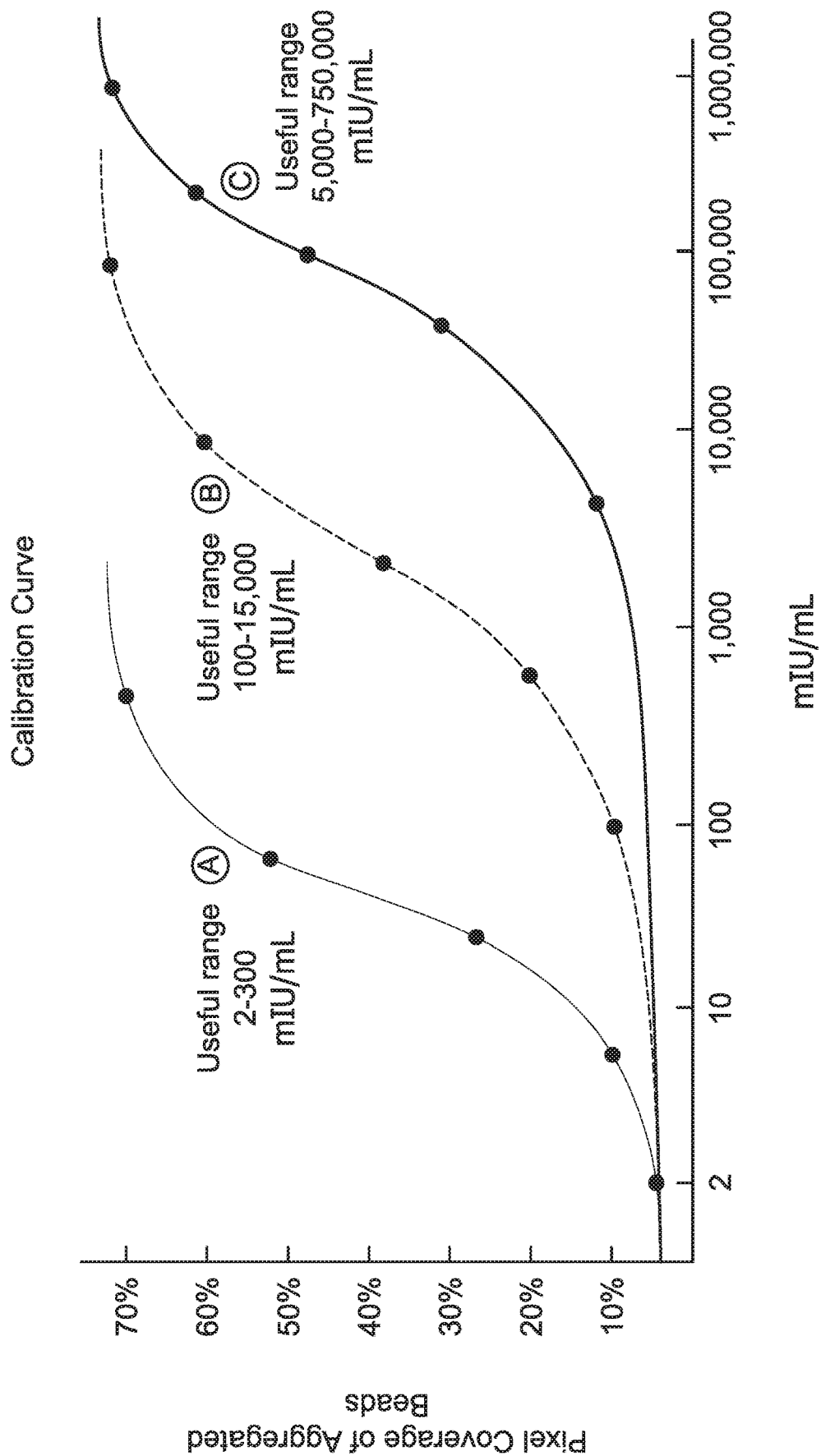
FIG. 11 shows an example plot of calibration curves for determining concentration of an analyte in a fluid sample based on coverage of an active sensor area by agglomerations of functionalized beads.
Figure 12:
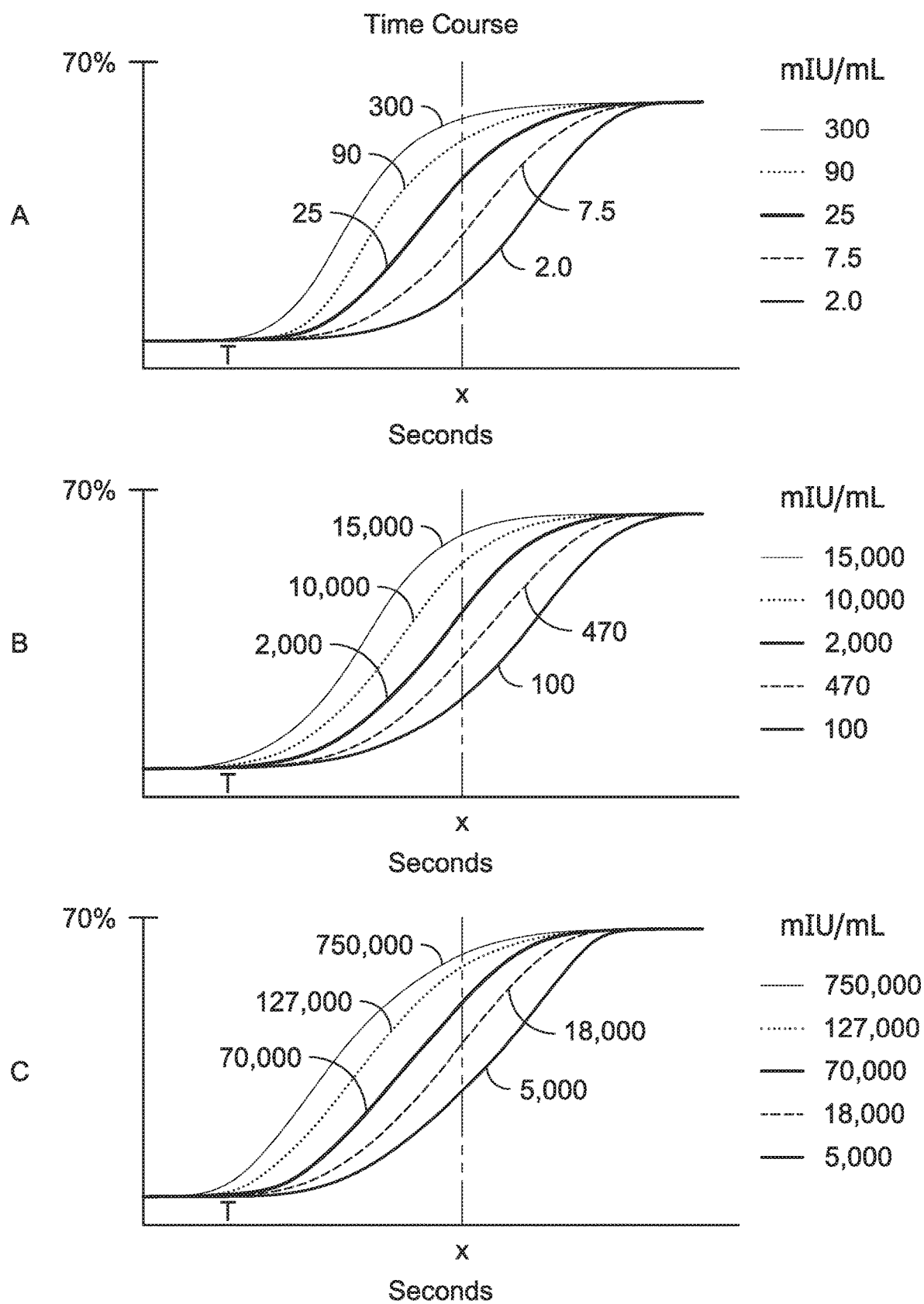
FIG. 12 shows example plots of coverage of active sensor areas by agglomerations of functionalized beads over time, wherein respective ones of the active sensor areas have respective sets of functionalized beads configured for detecting respective analyte concentration ranges.

Referring again to FIGS. 1A and 1B, the controller 110 is configured to cause the sensor 100 to (periodically or continuously) scan active sensor area 104 and active sensor area 204 with the plurality of sensor pixels 102 and sensor pixels 202. In an embodiment, the controller 110 is configured to cause the sensor 100 to perform multiple scans to detect growth rate of agglomerations 107 of functionalized beads 106 and agglomerations 207 of functionalized beads 206. The controller 110 can be configured to determine an absence of agglomerations of functionalized beads when no agglomerations of functionalized beads are detected by the sensor 100 (e.g., when functionalized beads do not agglutinate to a critical mass that is detectable by a sensor pixel of the sensor 100). In embodiments, the controller 110 is configured to determine various attributes of the fluid sample based on monitoring the agglomerations detected by the sensor 100. For example, the controller 110 can be configured to determine a concentration of at least one analyte in the fluid sample based on a coverage or change in coverage of active sensor area 104 by detected agglomerations 107 of functionalized beads 106, or a coverage or change in coverage of the active sensor area 204 by detected agglomerations 207 of functionalized beads 206. The controller 110 can be configured to track the coverage level and/or growth rate of the agglomerations based on signals periodically received by the controller 110 from sensor pixels 102 and sensor pixels 202. For example, the controller 110 can be configured to image active sensor area 104 and active sensor area 204. In some embodiments, the controller 110 is configured to collect sensor data at a rate of several frames per second. The controller 110 can be configured to generate a curve (or multiple curves) for respective ones of the active sensor areas (e.g., for active sensor area 104 and active sensor area 204) based on signals collected from sensor pixels 102 and sensor pixels 202 (e.g., based on tracking a number of sensor pixels 102/202 covered by agglomerations 107/207 of functionalized beads 106/206 over time). The controller 110 can also be configured to compare the curves with reference data (e.g., calibration curves) to determine a concentration of an analyte (or concentrations of multiple analytes) in a respective portion (e.g., portion 108 or portion 208) of the fluid sample or in different fluid samples. For example, FIGS. 11 and 12 show example calibration curves and collected data curves for coverage of active sensor areas (such as active sensor areas 104 and 204) by agglomerations of functionalized beads. For example, FIG. 12 shows data for a first sensor cell (A), a second sensor cell (B), and a third sensor cell (C).

The controller 110 can be configured to generate data and/or communication signals associated with assay results. In an embodiment, the controller 110 is configured to report an indication that the concentration of the analyte in the first portion 108 of the fluid sample is out of range when the level or rate of coverage of the first active sensor area 104 by agglomerations 107 of functionalized beads 106 fails to conform with a first reference data set or data plot (e.g., does not conform to a calibration curve). The controller 110 can also be configured to report a determined concentration of the analyte in the second portion 208 of the fluid sample when the level or rate of coverage of the first active sensor area 104 by agglomerations 107 of functionalized beads 106 fails to conform with a first reference data set or data plot, but the level or rate of coverage of the second active sensor area 204 by agglomerations 207 of functionalized beads 206 conforms with a second reference data set or data plot (e.g., is within a threshold level of allowable deviation from a calibration curve). The controller 110 can be configured to report a determined concentration of the analyte in the first portion 108 of the fluid sample when the level or rate of coverage of the first active sensor area 104 by agglomerations 107 of functionalized beads 106 conforms with a first reference data set or data plot, and also configured to report a determined concentration of the analyte in the second portion 208 of the fluid sample when the level or rate of coverage of the second active sensor area 204 by agglomerations 207 of functionalized beads 206 conforms with a second reference data set or data plot. In other embodiments, the controller 110 is configured to report at least one of a determined concentration of the analyte in the first portion 108 of the fluid sample or a determined concentration of the analyte in the second portion 208 of the fluid sample based on a first conformity between the level or rate of coverage of the first active sensor area 104 by agglomerations 107 of functionalized beads 106 and a first reference data set or data plot and a second conformity between the level or rate of coverage of the second active sensor area 204 by agglomerations 207 of functionalized beads 206 and a second reference data set or data plot. For example, the controller 110 can be configured to report a determined concentration of the analyte in the first portion 108 of the fluid sample or a determined concentration of the analyte in the second portion 208 based on which of the two assays shows higher sensitivity to the concentration of the analyte (e.g., a faster agglutination rate or better correspondence to one of the calibration curves). In another example, the controller 110 can report both results or an averaged or aggregate result (e.g., when both show high sensitivity, or when each shows higher sensitivity to a different analyte).

Figure 7A:
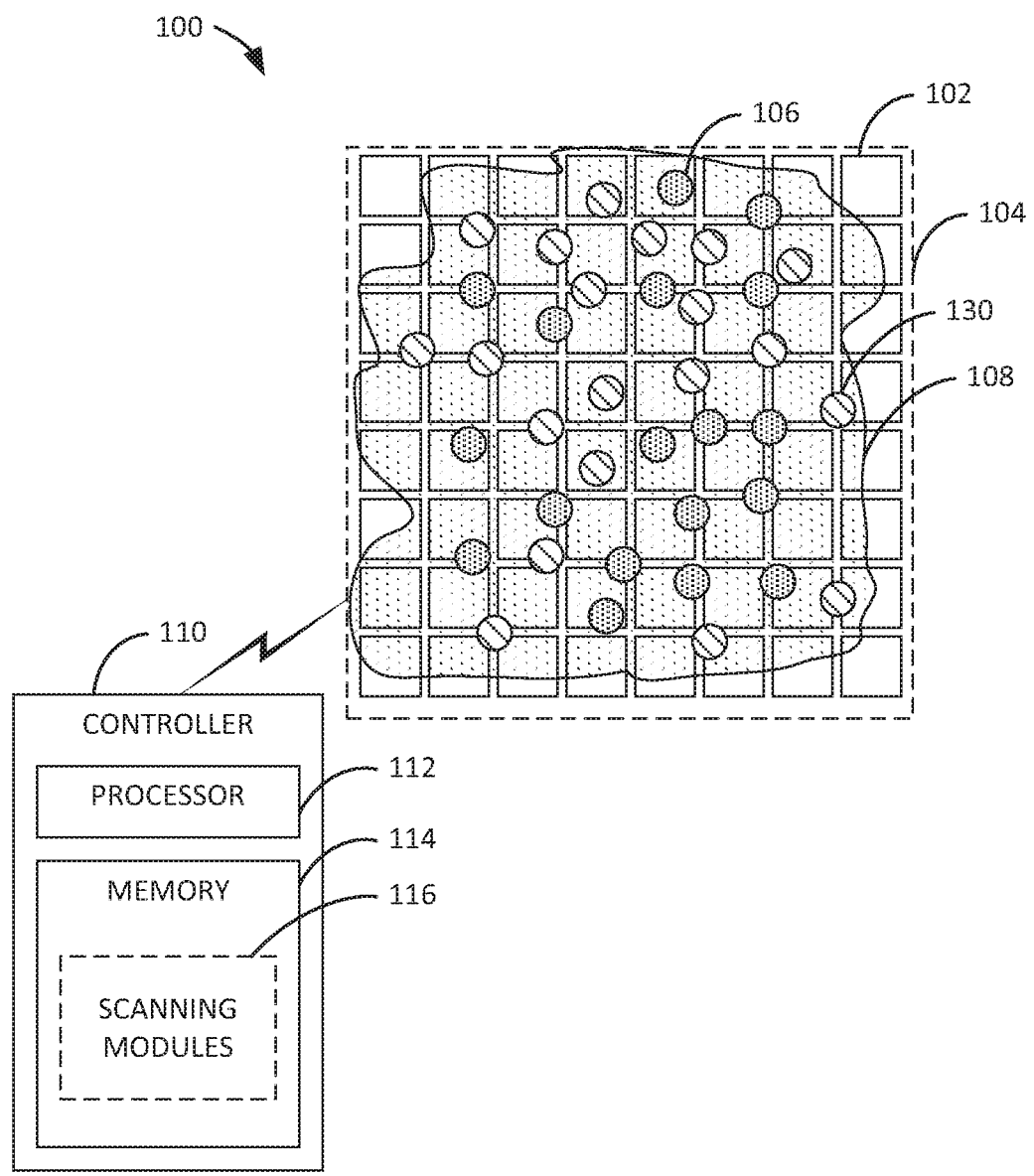
FIG. 7A is a schematic of a sensor having at least one active sensor area with a first plurality functionalized beads for performing a first agglutination assay and a second plurality of functionalized beads for performing a second agglutination assay, in accordance with an example embodiment of the present disclosure, wherein the first plurality of functionalized beads and the second plurality of functionalized beads are dispersed.
Figure 7B:
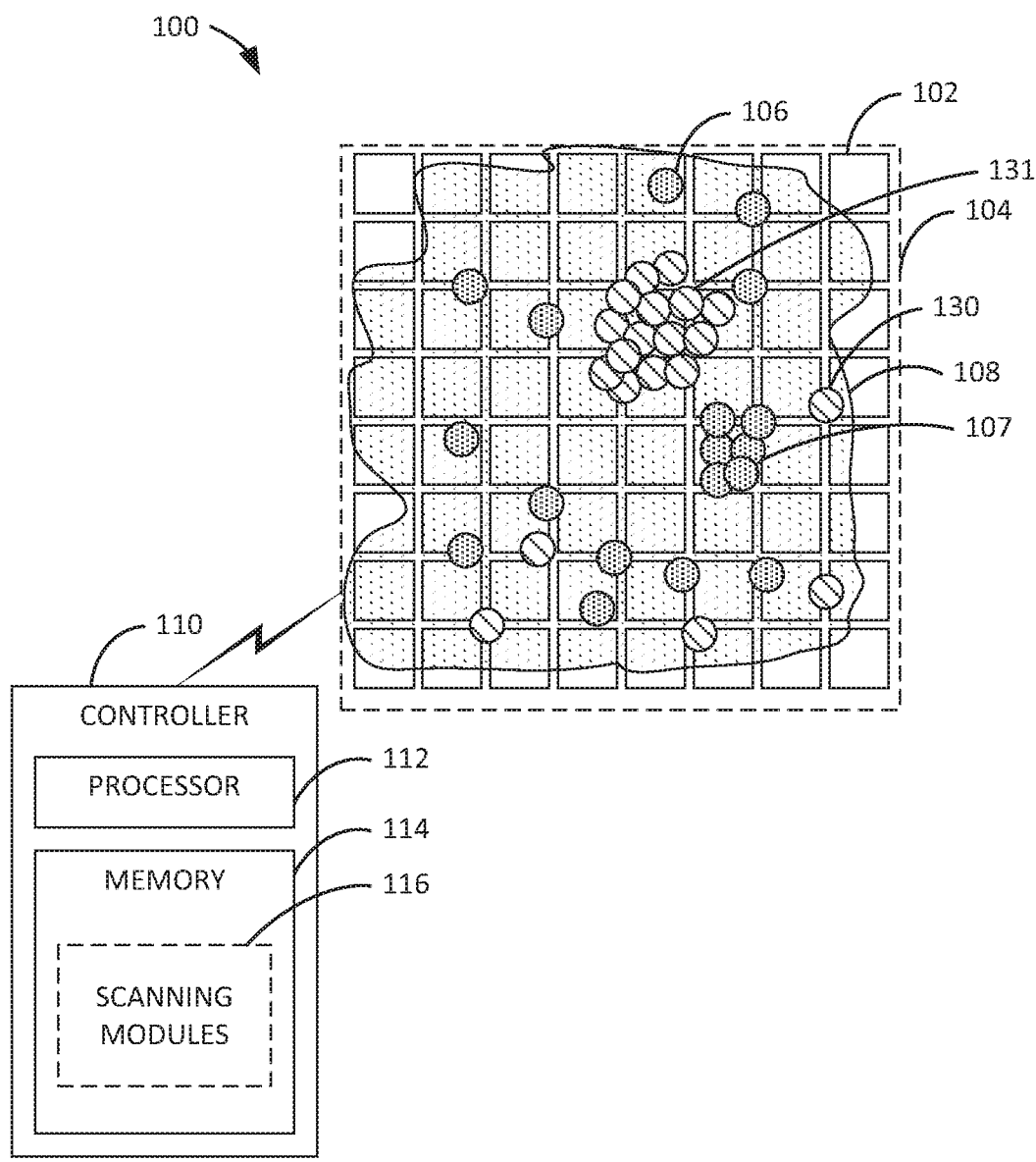
FIG. 7B is a schematic of a sensor having at least one active sensor area with a first plurality of functionalized beads for performing a first agglutination assay and a second plurality of functionalized beads for performing a second agglutination assay, in accordance with an example embodiment of the present disclosure, wherein the first plurality of functionalized beads and the second plurality of functionalized beads have formed respective agglomerations.

In embodiments shown in FIGS. 7A and 7B, the sensor 100 can employ multiple sets of functionalized beads (e.g., at least a first plurality of functionalized beads 106 and a second plurality of functionalized beads 130) in an active sensor area (e.g., in active sensor area 104). Functionalized beads 106 and functionalized beads 130 can have respective cross-sectional areas that are smaller than respective pixel areas defined by sensor pixel 102. Functionalized beads 106 and functionalized beads 130 can also have one or more physical parameters that are detectable by the sensor 100. In embodiments, functionalized beads 106 have at least one detectable physical parameter that is different from at least one detectable physical parameter of functionalized beads 130. Differentiating physical parameters that can be detected by the sensor 100 may include, but are not limited to, bead size, shape, color, optical properties (e.g., reflectance), magnetic properties (e.g., field strength), or electrical properties (e.g., conductance or impedance), combinations thereof, and so forth.

In embodiments, the controller 110 is configured to detect at least a first physical parameter associated with detected ones of functionalized beads 106 and at least a second physical parameter associated with detected ones of functionalized beads 130. The controller 110 is further configured to distinguish between functionalized beads 106 and functionalized beads 130 by comparing the first physical parameter and the second physical parameter to one or more stored physical parameters (e.g., stored in memory 114 or otherwise accessible by the controller 110). For example, the controller 110 can compare the electrical signals received from the sensor pixels 102 or the generated image, mapping, or data structure with a library of stored signal parameters, images, mappings, or data structures to distinguish functionalized beads 106 from functionalized beads 130.

The controller 110 can also be configured to determine assay results associated with functionalized beads 106 and functionalized beads 130 detected by the sensor pixels 102. FIG. 7A shows an example where functionalized beads 106 and functionalized beads 130 are both dispersed. Functionalized beads 106 and functionalized beads 130 can be functionalized differently from one another. For example, functionalized beads 106 and functionalized beads 130 can be configured to perform a first assay and a second assay, respectively. The first assay may be sensitive to a first analyte, while the second assay is sensitive to a second (different) analyte. For example, functionalized beads 106 can be configured to agglutinate (or remain dispersed) when a first analyte is present in the fluid sample 108, and functionalized beads 130 configured to agglutinate (or remain dispersed) when a second analyte is present. FIG. 7B shows an example where functionalized beads 106 and functionalized beads 130 both agglutinate, with functionalized beads 130 forming a larger agglomeration 131 than an agglomeration 107 formed by functionalized beads 106. This may indicate a faster reaction rate in association with (or due to) a higher concentration of an analyte associated with functionalized beads 131. In some embodiments, the functionalized beads 106 can include insulating beads with a high dielectric constant, while functionalized beads 130 can include conducting beads. The insulating beads (functionalized beads 106) can be functionalized to agglutinate in the presence of follicle stimulating hormone, while the conducting beads (functionalized beads 130) can be functionalized to agglutinate in the presence of estradiol. The sensor 100 can be configured to detect (e.g., image) agglomerations (clumping) of both types of beads. For example, the controller 110 can be configured to distinguish agglomerations 107 of functionalized beads 106 from agglomeration 131 of functionalized beads 106 based on the differences in conductivity which can affect impedance, capacitance, or magnetic field sensed by the sensor pixels 102.

The controller 110 can also be configured to determine an amount or concentration of detected analytes in the fluid sample 108. For example, the controller 110 can be configured to determine a concentration of a first analyte associated with a first assay performed with functionalized beads 106 based on a detected agglutination rate (i.e., rate of clumping), number, or size of detected agglomerations (i.e., clumps) of functionalized beads 106. Similarly, the controller 110 can be configured to determine a concentration of a second analyte associated with a second assay performed with functionalized beads 130 based on a detected agglutination rate, number, or size of detected agglomerations of functionalized beads 130. In some embodiments (e.g., as discussed previously discussed herein), the controller 110 can be configured to generate time lapse images based on multiple scans by the sensor pixels 102 in order to determine an agglutination rate or monitor growth of one or more detected agglomerations. The controller 110 can be further configured to generate a data curve based on the time lapse images and compare the data curve with one or more calibration curves to determine whether or not the data curve corresponds to an expected result, whereby the concentration of an analyte can be determined.

Example Process(es)

FIGS. 8A through 10B illustrate example processes 300, 400, and 500 for performing assays using functionalized beads (e.g., functionalized beads 106 and functionalized beads 206) that have respective cross-sectional areas that are smaller than respective pixel areas defined by sensor pixels (e.g., sensor pixels 102 and sensor pixels 202) of a sensor, such as the sensor 100 described herein and illustrated in FIGS. 1A through 7B. In general, operations of disclosed processes (e.g., processes 300, 400, and 500) may be performed in an arbitrary order, unless otherwise provided in the claims.

Figure 8A:
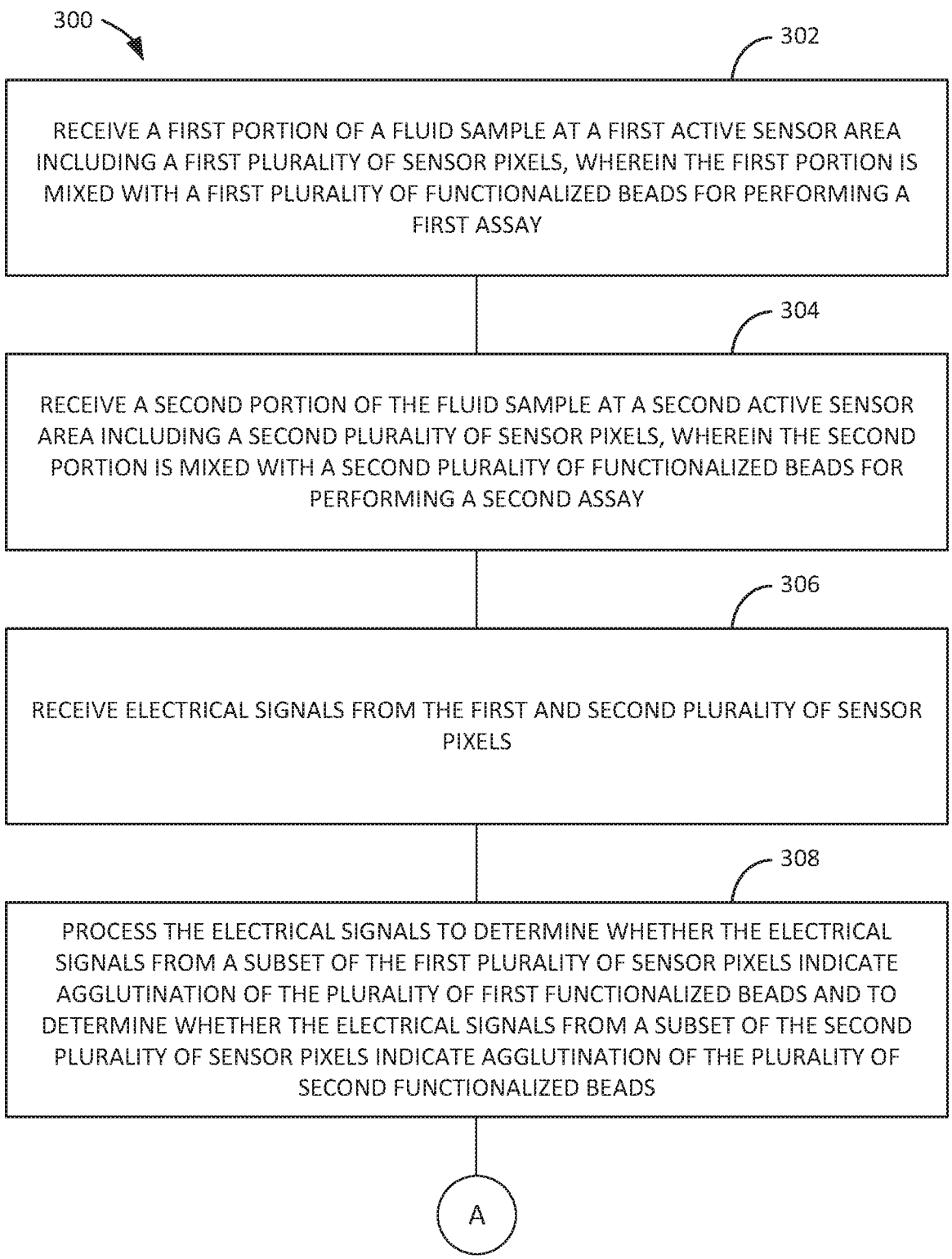
FIG. 8A is a partial flow diagram showing an example implementation of a method of detecting a concentration of a target analyte in a fluid sample with two or more active sensor areas, for example, using a sensor as illustrated in any of the preceding figures.
Figure 8B:
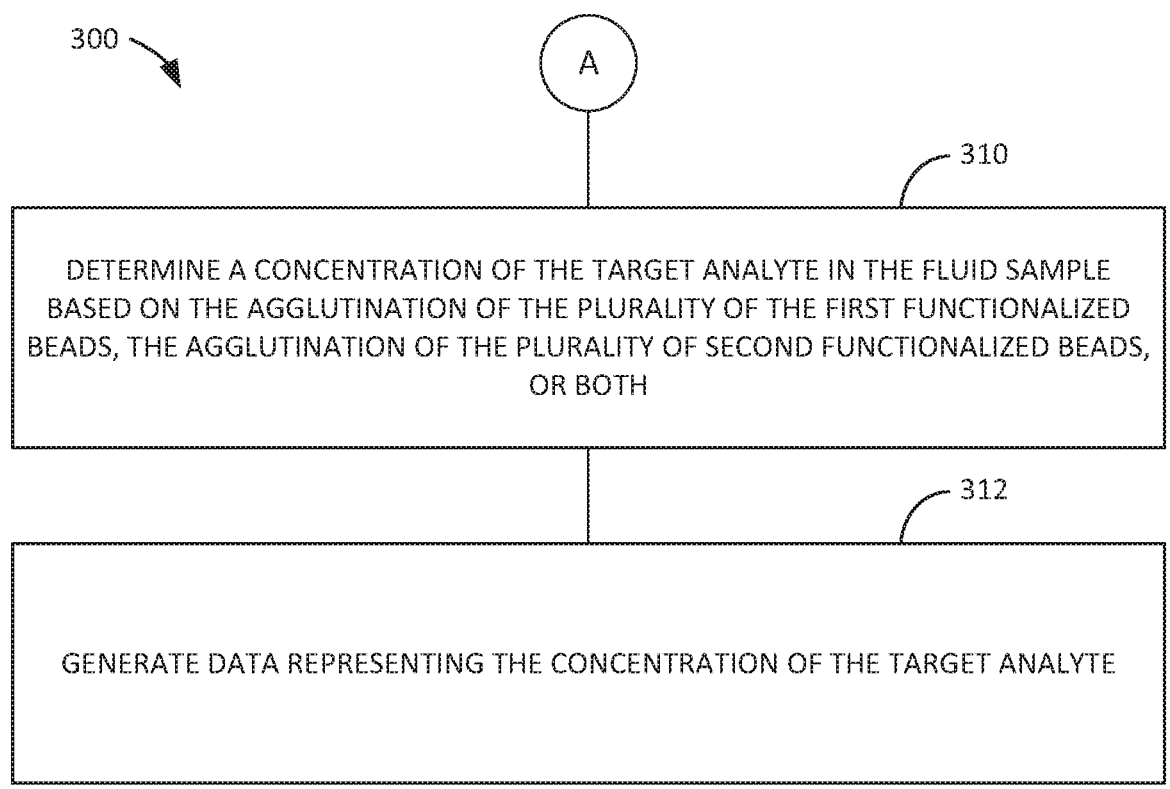
FIG. 8B is a partial flow diagram further illustrating the example implementation of the method shown in FIG. 8A.

Referring now to FIGS. 8A and 8B, in process 300 a first portion 108 of a fluid sample can be received at a first active sensor area 104 of the sensor 100 (block 302). The first portion 108 of the fluid sample can be mixed with a first plurality of functionalized beads 106 for performing a first assay. A second portion 208 of the fluid sample (or a second fluid sample) can be received at a second active sensor area 204 of the sensor 100 (block 304). The second portion 208 of the fluid sample can be mixed with a second plurality of functionalized beads 206 for performing a second assay. In implementations, the first assay and the second assay are configured to detect different concentration ranges of an analyte in the fluid sample. In some implementations, additional sensor cells can be employed (e.g., additional active sensor areas and respective sets of functionalized beads that may be configured differently from one another, such as a third active sensor area including a third plurality of sensor pixels, a fourth, and so on). The sensor 100 (e.g., via controller 110) can receive electrical signals from the first and second plurality of sensor pixels 102 and 202 (block 306). The controller 110 can process the electrical signals to determine whether the electrical signals from a subset 109 of the first plurality of sensor pixels 102 indicate agglutination of the plurality of the first functionalized beads 106 and to determine whether the electrical signals from a subset 209 of the second plurality of sensor pixels 202 indicate agglutination of the plurality of second functionalized beads 206 (block 308). For example, in the embodiment illustrated in FIG. 6B, the subset 109 of sensor pixels 102 (e.g., one or more of sensor pixels 102) can indicate agglutination of the first functionalized beads 106 based on electrical signals corresponding to a detected agglomeration 107 of beads 106, and the subset 209 of sensor pixels 202 (e.g., one or more of sensor pixels 202) can indicate agglutination of the second functionalized beads 206 based on electrical signals corresponding to a detected agglomeration 207 of beads 206. The controller 110 can determine a concentration of the target analyte in the fluid sample based on the agglutination of the plurality of the first functionalized beads 106, the agglutination of the plurality of the second functionalized beads 206, or both (block 310). For example, the controller 110 can be configured to determine a concentration of the target analyte in a respective portion of the fluid sample that is disposed in the first active sensor area 104, the second active sensor area 204, or both. In some embodiments, concentration measurements from the first active sensor area 104 and the second active sensor area 204 may be averaged or aggregated, or one of the measurements may be selected based on consistency, conformity to reference data, or the like. The controller 110 can then generate data representing the concentration of the target analyte (block 312). For example, the controller 110 may be configured to report a concentration value for the target analyte and/or generate a graphical depiction of the concentration value.

Figure 9:
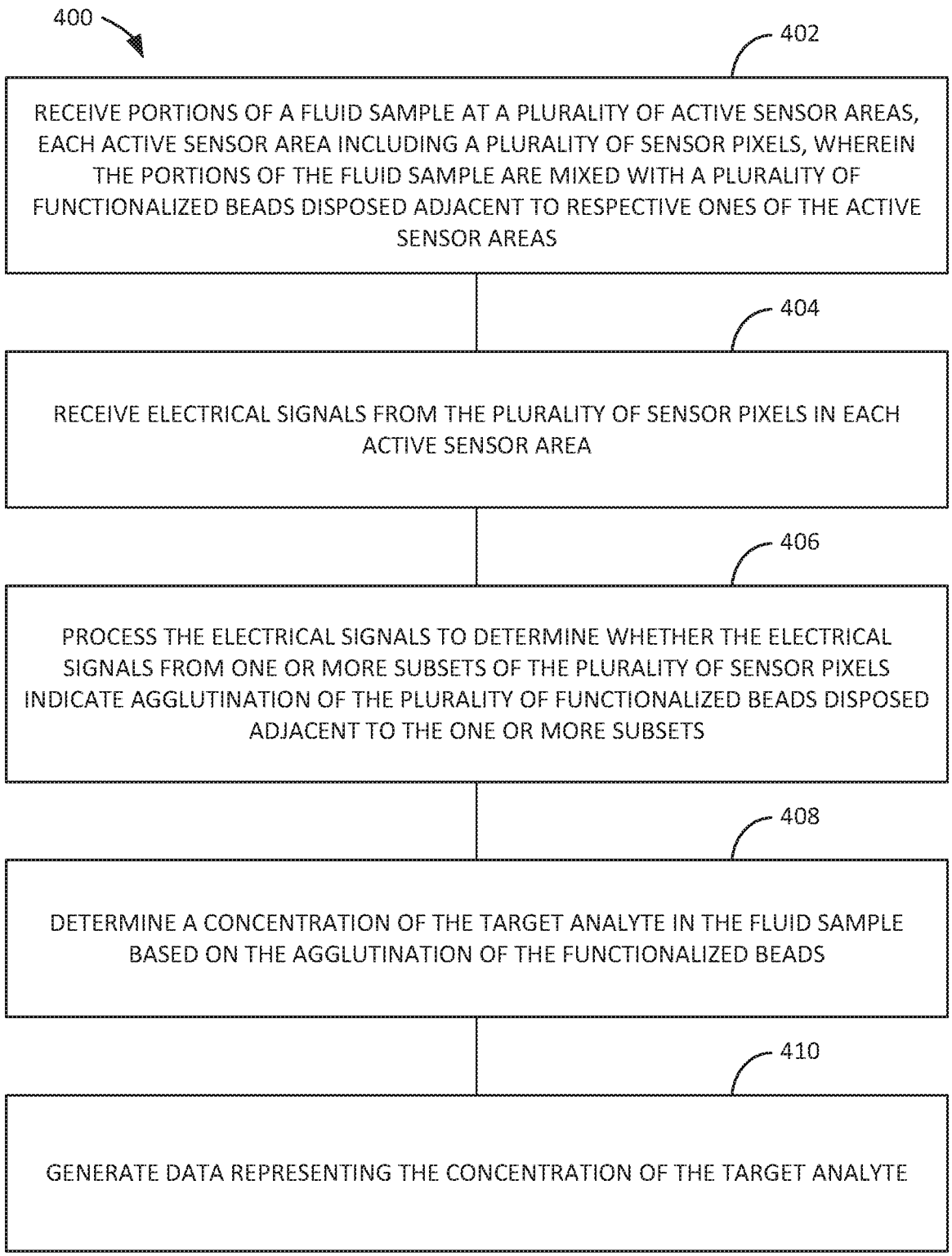
FIG. 9 is a flow diagram showing an example implementation of a method of detecting a concentration of a target analyte in a fluid sample with two or more active sensor areas, for example, using a sensor as illustrated in any of the preceding figures.

As shown in FIG. 9, in process 400 several portions (e.g., portions 108, 208, etc.) of a fluid sample can be received at a plurality of respective active sensor areas (e.g., active sensor area 104, 204, etc.) of the sensor 100 (block 402). The portions of the fluid sample can be mixed with respective sets of functionalized beads (e.g., functionalized beads 106, 206, etc.). The sensor 100 (e.g., via controller 110) can receive electrical signals from the plurality of sensor pixels (e.g., sensor pixels 102, 202, etc.) that make up the plurality of active sensor areas (block 404). The controller 110 can process the electrical signals to determine whether the electrical signals from one or more subsets (e.g., subset 109 and/or subset 209, etc.) of the plurality of sensor pixels (e.g., sensor pixels 102, 202, etc.) indicate agglutination of the plurality of the functionalized beads (e.g., functionalized beads 106, 206, etc.) (block 406). For example, in the embodiment illustrated in FIG. 6B, the subset 109 of sensor pixels 102 (e.g., one or more of sensor pixels 102) can indicate agglutination of the first functionalized beads 106 based on electrical signals corresponding to a detected agglomeration 107 of beads 106, and the subset 209 of sensor pixels 202 (e.g., one or more of sensor pixels 202) can indicate agglutination of the second functionalized beads 206 based on electrical signals corresponding to a detected agglomeration 207 of beads 206. The controller 110 can determine a concentration of the target analyte in the fluid sample based on the agglutination of the plurality of the functionalized beads (e.g., functionalized beads 106, 206, etc.) (block 408). The controller 110 can then generate data representing the concentration of the target analyte (block 410). For example, the controller 110 may be configured to report a concentration value for the target analyte and/or generate a graphical depiction of the concentration value.

Figure 10A:
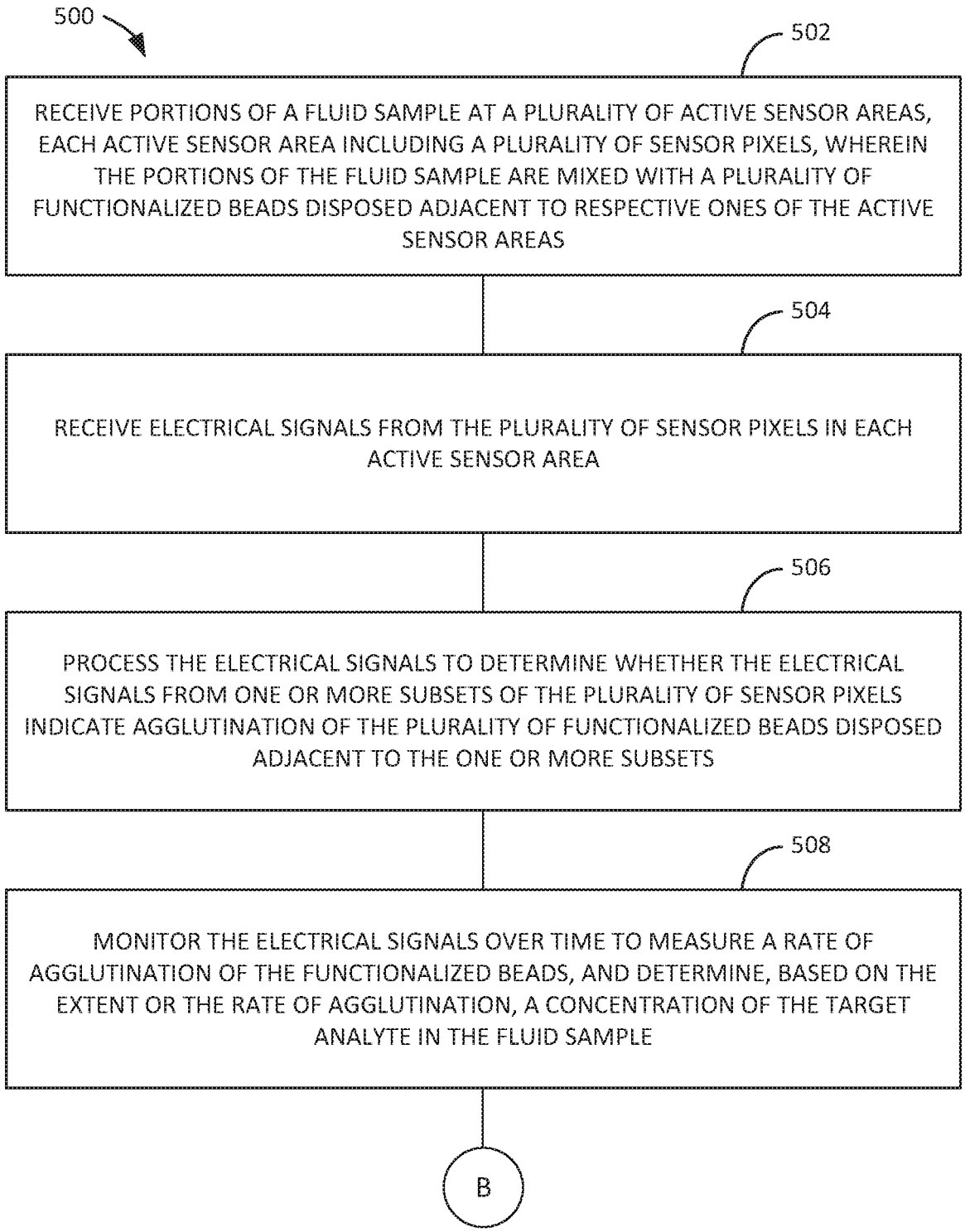
FIG. 10A is a partial flow diagram showing an example implementation of a method of detecting a concentration of a target analyte in a fluid sample with two or more active sensor areas, for example, using a sensor as illustrated in any of the preceding figures.
Figure 10B:
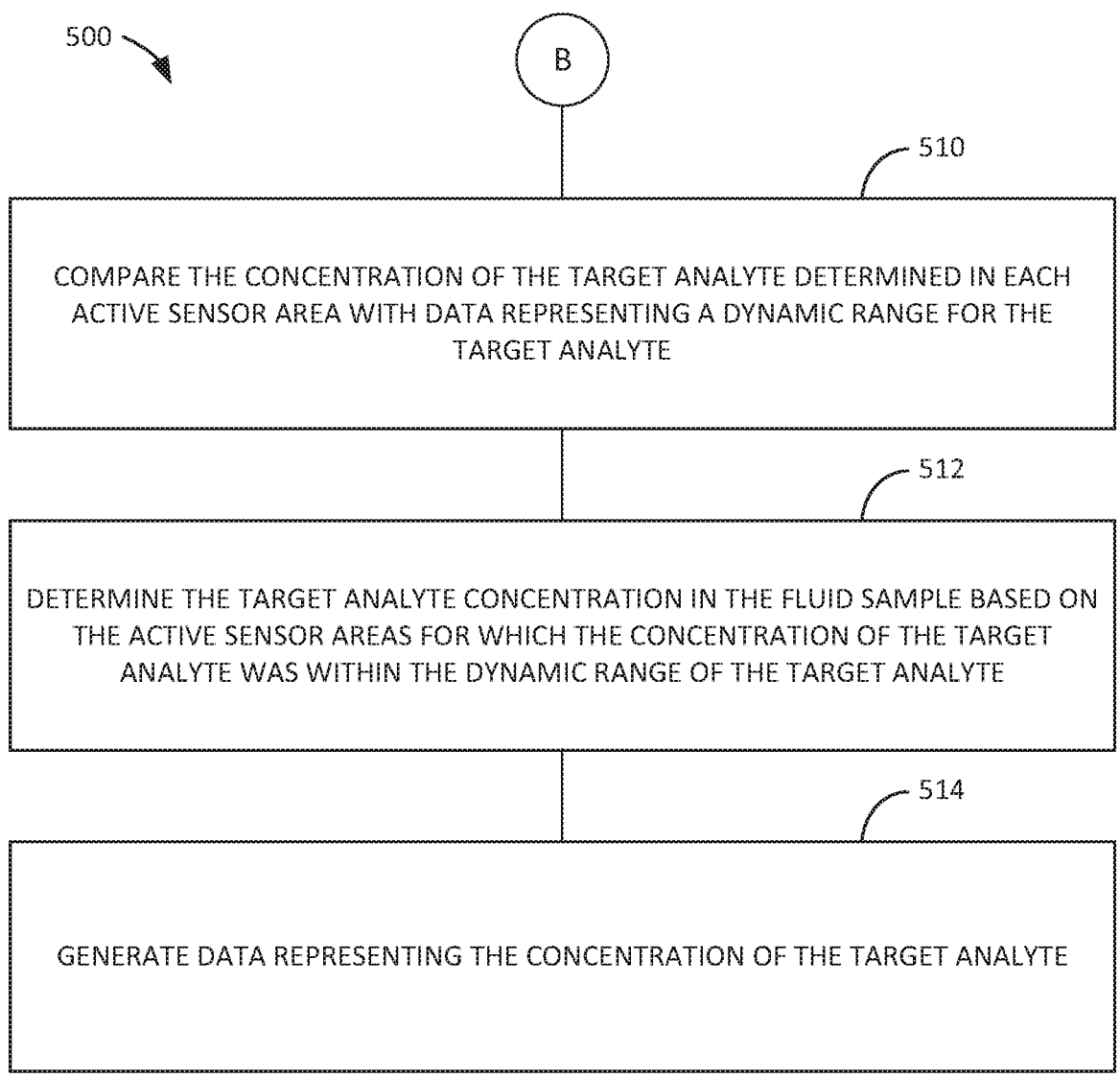
FIG. 10B is a partial flow diagram further illustrating the example implementation of the method shown in FIG. 10A.
Figure 13:
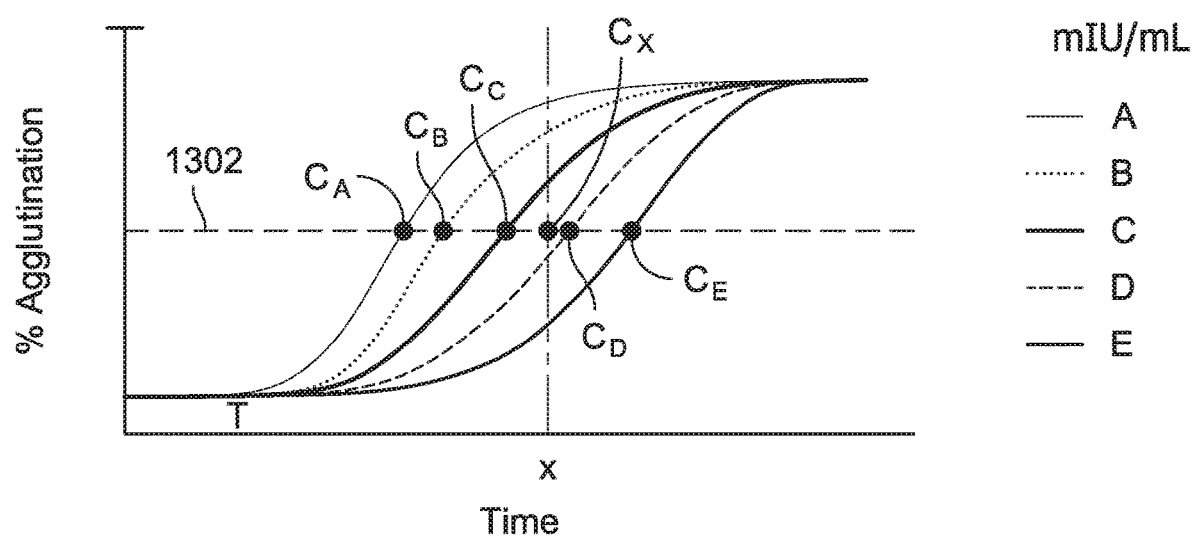
FIG. 13 shows a series of example sensitivity plots of coverage of active sensor areas by agglomerations of functionalized beads over time, wherein a plurality of reference plots associated with different sensitivities to concentrations of a target analyte are shown in comparison to a detected rate of agglutination at a point in time.

Another example process 500 is shown in FIGS. 10A and 10B, wherein the process tracks a rate of agglutination by monitoring electrical signals from a plurality of sensor pixels (e.g., sensor pixels 102, 202, etc.) over time. Several portions (e.g., portions 108, 208, etc.) of a fluid sample can be received at a plurality of respective active sensor areas (e.g., active sensor area 104, 204, etc.) of the sensor 100 (block 502). The portions of the fluid sample can be mixed with respective sets of functionalized beads (e.g., functionalized beads 106, 206, etc.). The sensor 100 (e.g., via controller 110) can receive electrical signals from the plurality of sensor pixels (e.g., sensor pixels 102, 202, etc.) that make up the plurality of active sensor areas (block 504). The controller 110 can process the electrical signals to determine whether the electrical signals from one or more subsets (e.g., subset 109 and/or subset 209, etc.) of the plurality of sensor pixels (e.g., sensor pixels 102, 202, etc.) indicate agglutination of the plurality of the functionalized beads (e.g., functionalized beads 106, 206, etc.) (block 506). For example, in the embodiment illustrated in FIG. 6B, the subset 109 of sensor pixels 102 (e.g., one or more of sensor pixels 102) can indicate agglutination of the first functionalized beads 106 based on electrical signals corresponding to a detected agglomeration 107 of beads 106, and the subset 209 of sensor pixels 202 (e.g., one or more of sensor pixels 202) can indicate agglutination of the second functionalized beads 206 based on electrical signals corresponding to a detected agglomeration 207 of beads 206. The controller 110 may monitor the electrical signals over time to measure a rate of agglutination of the functionalized beads, and determine, based on the rate of agglutination or the extent of agglutination, a concentration of the target analyte in the fluid sample (block 508). The controller 110 can compare the concentration of the target analyte determined in each active sensor area with data representing a dynamic range for the target analyte (block 510). For example, the controller 110 can compare the level or rate of coverage of the first active sensor area 108 by agglomerations 107 of functionalized beads 106 with reference data set or data plot (e.g., with a calibration curve, such as the calibration curve shown in FIG. 11) to determine a concentration of the analyte (or multiple analytes) in the first portion 108 of the fluid sample and/or can compare the level or rate of coverage of the second active sensor area 204 by agglomerations 207 of functionalized beads 206 with the reference data set or data plot (e.g., with a calibration curve, such as the calibration curve shown in FIG. 11) to determine a concentration of the analyte in the second portion 208 of the fluid sample. The controller 110 can be configured to determine the target analyte concentration in the fluid sample based on the active sensor areas for which the concentration of the target analyte was within the dynamic range of the target analyte (block 512). In an implementation, the sensor 100 collects multiple data points over time to generate a curve for the first active sensor area 108 and a curve for the second active sensor area 208 (e.g., such as the data curves shown in FIG. 12), and then compares the data curves to the calibration curves to determine whether or not a data curve conforms (e.g., has a threshold correspondence) to one of the calibration curves. For example, the data representing the dynamic range of the target analyte can be selected from a plurality of reference data sets or plots (e.g., such as plots A, B, C, D, and E shown in FIG. 13). Referring to FIG. 13, the reference data set or plot that represents the dynamic range of the target analyte can be selected by comparing the rate of agglutination of the target analyte in the fluid sample to the plurality of reference data sets or data plots (e.g., plots A, B, C, D, and E) and selecting a reference data set or data plot (e.g., plot D) having an inflection point ($C_D$) that is nearest to the rate of agglutination ($C_X$) of the target analyte in the fluid sample. For example, FIG. 13 shows a line 1302 that goes through inflection points $C_A$, $C_B$, $C_C$, $C_D$, and $C_E$ of plots A, B, C, D, and E, respectively. As can be seen, the inflection point $C_D$ of plot D is the closest to the rate of agglutination $C_X$ detected by the sensor at time X. Based on such a comparison, the controller 110 can be configured to select plot D as the data representing the dynamic range of the target analyte, where the points at which the plot plateaus or becomes substantially flat can indicate endpoints of the dynamic range of the target analyte. After determining the target analyte concentration based on the active sensor areas for which the concentration of the target analyte was within the dynamic range of the target analyte, the controller 110 can generate data representing the concentration of the target analyte (block 514). For example, the controller 110 may be configured to report a concentration value for the target analyte and/or generate a graphical depiction of the concentration value.

The various functions, operations, blocks, or steps described throughout the present disclosure may be carried out in any order, by any combination of hardware, software, or firmware. For example, controller 110 may be configured to execute one or more blocks of method 300. In embodiments, the controller 110 can include one or more of the following: electronic circuitry, logic gates, multiplexers, a programmable logic device, an application-specific integrated circuit (ASIC), a controller/microcontroller, or a computing system. The controller 110 can include any device having at least one processor (e.g., processor 112) configured to execute program instructions (e.g., software modules, such as scanning modules 116) from a carrier medium (e.g., memory 114).

CONCLUSION

It is to be understood that the present application is defined by the appended claims. Although embodiments of the present application have been illustrated and described herein, it is apparent that various modifications may be made by those skilled in the art without departing from the scope and spirit of this disclosure.

What is claimed is:

1. A sensor assembly, comprising:
   a chamber configured to receive a fluid sample;
   a first active sensor area disposed in a first portion of the chamber and configured to receive a first portion of the fluid sample, and including
      a first surface having a first plurality of sensor pixels, each sensor pixel having a first pixel area, and
      first functionalized insulating beads disposed on the first surface, respective ones of the first functionalized insulating beads having a cross-sectional area that is smaller than the first pixel area and having a first coating configured to cause agglutination of a plurality of the first functionalized beads when a target analyte is present in the first portion of the fluid sample;
   a second active sensor area disposed in a second portion of the chamber and configured to receive a second portion of the fluid sample, and including
      a second surface having a second plurality of sensor pixels, each sensor pixel having a second pixel area, and
      second functionalized conducting beads disposed on the second surface, respective ones of the second functionalized conducting beads having a cross-sectional area that is smaller than the second pixel area and having a second coating configured to cause agglutination of a plurality of the second functionalized beads when the target analyte is present in the second portion of the fluid sample; and
   a controller configured to
      receive electrical signals from the first and second plurality of sensor pixels,
      process the electrical signals to determine whether the electrical signals from a subset of the first plurality of sensor pixels indicate agglutination of the plurality of the first functionalized beads on the first surface over the subset of the first plurality of sensor pixels and to determine whether the electrical signals from a subset of the second plurality of sensor pixels indicate agglutination of the plurality of second functionalized beads on the second surface over the subset of the second plurality of sensor pixels, and
      determine a concentration of the target analyte in the fluid sample based on the agglutination of the plurality of the first functionalized beads, the agglutination of the plurality of the second functionalized beads, or both; and
      generate data representing the concentration of the target analyte.

2. The sensor assembly of claim 1, wherein the controller is configured to determine the concentration of the target analyte in the fluid sample at least in part by
   determining a number of sensor pixels in the subset of the first plurality of sensor pixels that indicate agglutination of the plurality of the first functionalized beads,
   determining a number of sensor pixels in the subset of the second plurality of sensor pixels that indicate agglutination of the plurality of the second functionalized beads, or
   determining the number of sensor pixels in the subset of the first plurality of sensor pixels that indicate agglutination of the plurality of the first functionalized beads and the number of sensor pixels in the subset of the second plurality of sensor pixels that indicate agglutination of the plurality of the second functionalized beads.

3. The sensor assembly of claim 1, wherein the controller is configured to determine the concentration of the target analyte in the fluid sample at least in part by
   determining a first rate of agglutination corresponding to a number of sensor pixels in the subset of the first plurality of sensor pixels that indicate agglutination of the plurality of the first functionalized beads over time,
   determining a second rate of agglutination corresponding to a number of sensor pixels in the subset of the second plurality of sensor pixels that indicate agglutination of the plurality of the second functionalized beads over time, or
   determining the first rate of agglutination corresponding to the number of sensor pixels in the subset of the first plurality of sensor pixels that indicate agglutination of the plurality of the first functionalized beads over time and the second rate of agglutination corresponding to the number of sensor pixels in the subset of the second plurality of sensor pixels that indicate agglutination of the plurality of the second functionalized beads over time.

4. The sensor assembly of claim 3, wherein the controller is further configured to compare the first rate of agglutination, the second rate of agglutination, or both the first rate of agglutination and the second rate of agglutination with a reference data set or data plot to determine the concentration of the target analyte in the fluid sample.

5. The sensor assembly of claim 1, wherein the controller is configured to determine the concentration of the target analyte in the fluid sample at least in part by
   identifying and quantifying signal measurements from adjacent sensor pixels in the subset of the first plurality of sensor pixels that indicate agglutination of the plurality of the first functionalized beads,
   identifying and quantifying signal measurements from adjacent sensor pixels in the subset of the second plurality of sensor pixels that indicate agglutination of the plurality of the second functionalized beads, or
   identifying and quantifying signal measurements from adjacent sensor pixels in the subset of the first plurality of sensor pixels that indicate agglutination of the plurality of the first functionalized beads and identifying and quantifying signal measurements from adjacent sensor pixels in the subset of the second plurality of sensor pixels that indicate agglutination of the plurality of the second functionalized beads.

6. The sensor assembly of claim 1, wherein the controller is configured to determine the concentration of the target analyte in the fluid sample at least in part by
   determining a first rate of agglutination corresponding to quantified signal measurements from adjacent sensor pixels in the subset of the first plurality of sensor pixels that indicate agglutination of the plurality of the first functionalized beads over time,
   determining a second rate of agglutination corresponding to quantified signal measurements from adjacent sensor pixels in the subset of the second plurality of sensor pixels that indicate agglutination of the plurality of the second functionalized beads over time, or determining the first rate of agglutination corresponding to the quantified signal measurements from adjacent sensor pixels in the subset of the first plurality of sensor pixels that indicate agglutination of the plurality of the first functionalized beads over time and the second rate of agglutination corresponding to the quantified signal measurements from adjacent sensor pixels in the subset of the second plurality of sensor pixels that indicate agglutination of the plurality of the second functionalized beads over time.

7. The sensor assembly of claim 6, wherein the controller is further configured to compare the first rate of agglutination, the second rate of agglutination, or both the first rate of agglutination and the second rate of agglutination with a reference data set or data plot to determine the concentration of the target analyte in the fluid sample.

8. The sensor assembly of claim 1, wherein the first active sensor area is configured to perform a first assay and the second active sensor area is configured to perform a second assay, wherein the first assay and the second assay are sensitive to different ranges of concentrations of the target analyte.

9. The sensor assembly of claim 8, wherein the first functionalized beads have different dimensions than the second functionalized beads in order to detect the different ranges of concentrations of the target analyte.

10. The sensor assembly of claim 8, wherein the first functionalized beads have a different composition than the second functionalized beads in order to detect the different ranges of concentrations of the target analyte.

11. The sensor assembly of claim 8, wherein the first functionalized beads are coated with a different amount of a reagent than the second functionalized beads in order to detect the different ranges of concentrations of the target analyte.

12. The sensor assembly of claim 8, wherein the first functionalized beads are coated with a different reagent than the second functionalized beads in order to detect the different ranges of concentrations of the target analyte.

13. The sensor assembly of claim 8, wherein the first pixel area is different from the second pixel area in order to detect the different ranges of concentrations of the target analyte.

14. The sensor assembly of claim 13, wherein the first pixel area is larger than the second pixel area.

15. The second assembly of claim 14, wherein each sensor pixel of the first plurality of sensor pixels comprises a software-defined sensor pixel that includes at least two sensor pixels.

16. The sensor assembly of claim 1, further comprising:
a substrate supporting the first active sensor area and the second active sensor area; and
a cap structure disposed on the substrate over the first active sensor area and the second active sensor area, the cap structure and substrate cooperating to form the chamber so that the first active sensor area and the second active sensor area are disposed within the chamber.

17. The sensor assembly of claim 16, further comprising at least one reagent coating disposed within the chamber on at least one of the substrate over one or both of the first active sensor area and the second active sensor area or the cap structure, the at least one reagent coating comprising at least one of the first functionalized beads and the second functionalized beads, wherein at least one of the first functionalized beads and the second functionalized beads are configured to be released from the at least one reagent coating when the fluid sample is received in the chamber.

18. An analyte sensor, comprising:
a chamber configured to receive a fluid sample;
a plurality of active sensor areas, each active sensor area being disposed in a different portion of the chamber and configured to receive a portion of the fluid sample;
each active sensor area including a surface having a plurality of sensor pixels, each sensor pixel having a pixel area, and each sensor pixel being configured to generate an electrical signal indicative of change in an electric field;
a plurality of functionalized beads disposed in the different portions of the chamber, the plurality of functionalized beads including a first set of beads disposed on a first surface and a second set of beads disposed on a second surface, the first set of beads disposed on the first surface being insulating beads and the second set of beads disposed on the second surface being conducting beads, each functionalized bead of the plurality of functionalized beads including a cross-sectional area that is smaller than the pixel area and a coating configured to cause agglutination of at least a portion of the plurality of functionalized beads with each other when a target analyte is present in the portion of the fluid sample; and
a controller being configured to
receive the electrical signals from the plurality of sensor pixels in each active sensor area,
process the electrical signals to determine whether the electrical signals from one or more subsets of the plurality of sensor pixels are indicative of agglutination of the functionalized beads disposed adjacent to the one or more subsets,
determine a concentration of the target analyte in the fluid sample based on the agglutination of the functionalized beads, and
generate data representing the concentration of the target analyte.

19. The analyte sensor of claim 18, wherein the electric field is at least one of a vertical electric field, a horizontal electric field, or an oscillating electric field.

20. The analyte sensor of claim 18, wherein the electric field is an oscillating electric field having a frequency in the range of 1 megahertz and 300 megahertz.

21. A sensor, comprising:
a chamber configured to receive a fluid sample;
a plurality of active sensor areas, each active sensor area being disposed in a different portion of the chamber and configured to receive a portion of the fluid sample;
each active sensor area including a surface having a plurality of sensor pixels being configured in an array, each sensor pixel having a pixel area;
a plurality of functionalized beads disposed in the different portions of the chamber, the plurality of functionalized beads including a first set of beads disposed on a first surface and a second set of beads disposed on a second surface, the first set of beads disposed on the first surface being insulating beads and the second set of beads disposed on the second surface being conducting beads, each functionalized bead of the plurality of functionalized beads including a cross-sectional area that is smaller than the pixel area and a coating configured to cause agglutination of at least a portion of the plurality of functionalized beads with each other when a target analyte is present in the fluid sample; and a controller configured to
- receive from each active sensor area, electrical signals from the plurality of sensor pixels in the active sensor area,
- process the electrical signals to determine whether the electrical signals from one or more subsets of the plurality of sensor pixels are indicative of agglutination of the functionalized beads disposed adjacent to the one or more subsets,
- monitor the electrical signals over time to measure a rate of agglutination of the functionalized beads, and determine, based on the rate of agglutination, a concentration of the target analyte in the fluid sample,
- compare the concentration of the target analyte determined in each active sensor area with data representing a dynamic range for the target analyte,
- determine target analyte concentration in the fluid sample based on the active sensor areas for which the concentration of the target analyte was within the dynamic range of the target analyte, and
- generate data representing the target analyte concentration.

22. The sensor of claim 21, wherein the data representing the dynamic range for the target analyte is selected from a plurality of reference data sets or data plots by comparing the rate of agglutination of the target analyte in the fluid sample to the plurality of reference data sets or data plots and selecting a reference data set or data plot having an inflection point that is nearest to the rate of agglutination of the target analyte in the fluid sample.

* * * * *